United States Patent [19]
Herb et al.

[11] Patent Number: 5,942,216
[45] Date of Patent: *Aug. 24, 1999

[54] WATER-IN-OIL-IN-WATER COMPOSITIONS

[75] Inventors: Craig A. Herb, Chicago; Liang Bin Chen, Lombard; Judy B. Chung, Glenview; Michelle A. Long, Lombard; Wei Mei Sun, Palatine, all of Ill.

[73] Assignee: Helene Curtis, Inc., Chicago, Ill.

[*] Notice: This patent is subject to a terminal disclaimer.

[21] Appl. No.: 08/804,365

[22] Filed: Feb. 21, 1997

Related U.S. Application Data

[63] Continuation of application No. 08/349,904, Dec. 6, 1994, Pat. No. 5,565,280.

[51] Int. Cl.$^6$ .............................. A61K 7/13; A61K 7/42; A61K 9/113; B01J 13/00
[52] U.S. Cl. ................................ 424/70.28; 8/405; 8/406; 8/421; 8/501; 424/70.121; 424/70.19; 424/70.2; 424/70.24; 424/70.6; 424/401; 514/937; 514/975; 516/54
[58] Field of Search ..................................... 252/312, 314; 8/405, 406, 421, 501; 424/401, 70.121, 70.19, 70.24, 70.28, 70.6, 59, DIG. 2, 70.2; 514/937, 975; 516/54

[56] References Cited

U.S. PATENT DOCUMENTS

| | | | |
|---|---|---|---|
| 3,630,654 | 12/1971 | Rosenthal et al. | 424/70.6 X |
| 4,169,704 | 10/1979 | Fakhouri | 8/421 |
| 4,254,105 | 3/1981 | Fukuda | 514/762 |
| 4,767,625 | 8/1988 | Mitsuno et al. | 424/401 |
| 4,940,576 | 7/1990 | Walsh | 424/70.24 X |
| 5,034,218 | 7/1991 | Duvel | 424/70.19 X |
| 5,059,414 | 10/1991 | Dallal et al. | 424/70.2 |
| 5,304,334 | 4/1994 | Lahanas et al. | 424/78.03 X |
| 5,478,561 | 12/1995 | Ferrero | 424/401 |
| 5,656,280 | 8/1997 | Herb et al. | 424/401 |

*Primary Examiner*—Richard D. Lovering
*Attorney, Agent, or Firm*—Matthew Boxer

[57] ABSTRACT

Water-in-oil-in-water multiple emulsion compositions are disclosed. The multiple emulsion compositions comprise an external aqueous phase optionally incorporating a surfactant system capable of forming liquid crystals as an emulsifier. The internal phase comprises a primary water-in-oil emulsion, wherein the primary emulsion comprises a first topically-active compound, a surfactant phase, an oil phase, and water.

55 Claims, No Drawings

WATER-IN-OIL-IN-WATER COMPOSITIONS

CROSS-REFERENCE TO RELATED APPLICATION

This application is a continuation of U.S. patent application Ser. No. 08/349,904, filed Dec. 6, 1994, now U.S. Pat. No. 5,565,280 issued Aug. 12, 1997.

FIELD OF THE INVENTION

The present invention is directed to water-in-oil-in-water ($W_1$-O-$W_2$) multiple emulsion compositions comprising: (1) a primary water-in-oil ($W_1$/O) emulsion as the internal phase and (2) an external aqueous phase. The primary $W_1$/O emulsion comprises (a) a first topically-active compound; (b) a surfactant or blend of surfactants; (c) an oil phase comprising a silicone compound, a hydrocarbon compound or a mixture thereof; and (d) water. The external aqueous phase comprises water and an emulsifier comprising a surfactant system capable of forming stabilizing liquid crystals. The external aqueous phase preferably further comprises a second topically-active compound. In use, a $W_1$-O-$W_2$ multiple emulsion composition is applied to the skin or hair to deliver the second topically-active compound. The external aqueous phase of the composition can be rinsed from or allowed to remain on the skin or hair. The primary ($W_1$/O) emulsion deposits on and remains on the hair or skin. After evaporation of the oil phase or after rupture of the $W_1$/O emulsion by friction (e.g., rubbing), the first topically-effective compound remains on the skin or hair to perform its intended function.

BACKGROUND OF THE INVENTION

An ideal composition for delivery of a topically-active compound to skin or hair delivers the topically-active compound such that it adheres to the skin or hair, while topically-inactive ingredients evaporate or are rinsed from the application site. Delivery of a water-insoluble topically-active compound is facilitated because the topically-active compound is not removed from the application site during the rinsing step. The difficulty with this type of composition resides in incorporating the water-insoluble topically-active compound into an aqueous composition. This difficulty is overcome by forming emulsions. Therefore, topically-active compounds, such as a hair conditioner, a hair dye, a skin care compound or a topical medicament, conventionally have been delivered from either oil-in-water emulsions or water-in-oil emulsions.

With respect to water-soluble and water-dispersible topically-active compounds (hereinafter collectively termed "water-soluble topically-active compounds"), it is easy to incorporate the topically-active compound into an aqueous composition. However, a substantial amount, or all, of the water-soluble compound can be rinsed from the treated skin or hair. The water-soluble compound therefore cannot perform its intended function and is wasted. Accordingly, rinse-off compositions often incorporate an excess of the water-soluble topically-active compound, such that a sufficient amount of the compound remains on the skin or hair after rinsing to perform its intended function. This problem is not encountered with leave-on compositions.

Similarly, two-in-one products, like shampoo-conditioner compositions, have been difficult to formulate not only because of the water solubility of many quaternary ammonium compounds, but also because of the well-known incompatibility between an anionic surfactant and a quaternary ammonium compound. Formulators either have avoided this problem by sequentially contacting the hair first with an anionic surfactant composition, then a quaternary ammonium compound composition, or have overcome this problem by using silicone conditioners in shampoo-conditioners. However, silicones and similar conditioners are water insoluble and an esthetically-unpleasant residue builds up on the hair after repeated applications. In addition, quaternary ammonium compounds impart hair conditioning properties different from a silicone, and therefore it is desirable to condition the hair with quaternary ammonium compounds in place of, or in conjunction with, a silicone.

Investigators therefore have searched for topically-effective compositions that overcome the above-described disadvantages, and that have consumer-acceptable stability and esthetics. Rinse-off, topically-effective compositions however often are difficult to formulate because of the water solubility of the desired topically-active compound. Leave-on, topically effective compositions are difficult to formulate because of the incompatibility between various topically-active compositions.

One type of composition that has been investigated to overcome these problems are multiple emulsions. Multiple emulsions are complex emulsions of emulsions formed by dispersing droplets in a continuous phase, wherein the droplets themselves contain smaller droplets of a liquid similar to the external continuous phase. One type of multiple emulsion is a water-in-oil-in-water emulsion ($W_1$-O-$W_2$), wherein a primary water-in-oil ($W_1$/O) emulsion is dispersed in an external aqueous phase ($W_2$). Multiple emulsions also are known as liquid membrane systems because, in the case of a $W_1$-O-$W_2$ emulsion, an organic membrane, film or layer separates the inner water droplets from the external aqueous phase.

$W_1$-O-$W_2$ multiple emulsion compositions have been used in the pharmaceutical industry as vaccine adjuvants and as sustained release and parental drug delivery systems. However, the low stability of $W_1$-O-$W_2$ multiple emulsion compositions has limited their widespread use.

Multiple emulsion compositions also have been used in cosmetics and skin care products. $W_1$-O-$W_2$ multiple emulsions however were difficult to prepare and were unstable at elevated temperatures. In addition, various active ingredients had a tendency to further destabilize the multiple emulsions, for example causing leakage between the external aqueous phase and internal aqueous phase.

$W_1$-O-$W_2$ multiple emulsion compositions have been disclosed in numerous patents and publications. For example, M. C. Taelman et al., "Multiple Emulsions in Cosmetics", Publication RP112/94E, March, 1994, ICI Europe Limited, Everberg, Belgium, discloses multiple emulsions in general, including methods of manufacturing multiple emulsions. S. Matsumoto et al., *J. Dispersion Science and Technology*, 10 (1989), pp. 455–482, discloses the use of multiple emulsions in the food, drug and cosmetic industries.

Other publications which disclose multiple $W_1$-O-$W_2$ emulsions are:

S. S. Davis et al., *Encyclopedia of Emulsion Technology*, Vol. 2; P. Becher, Ed.; Marcel Dekker, Inc., New York, N.Y. (1985), pp. 159–238;

Y. Sela et al., *Colloids and Surfaces A: Physicochemical and Engineering Aspects*, 83 (1994), pp. 143–150;

K. Oza et al., *J. Dispersion Science and Technology*, 10(2) (1985), pp. 163–185;

J. Zatz et al., *J. Soc. Cosmet. Chem.*, 39 (May/June 1988), pp. 211–222;

C. Fox, *Cosmetics and Toiletries*, 101 (November 1986), pp. 101–106 and 109–112

M. deluca et al., *Cosmetics and Toiletries*, 105 (November 1990), pp. 65–66 and 69;

T. Tadros, "Application of Multiple Emulsions in Cosmetics", ICI Surfactant publication RP56/92E (1992); and C. Prybilsky et al., *Cosmetics and Toiletries*, 106 (November 1991), pp. 97–100.

Various patents disclose multiple emulsion compositions used in cosmetic compositions. For example, WO 94/01073 discloses gelled multiple emulsion compositions for cosmetic use. Other patents include WO 94/02120; WO 93/00160; WO 92/18227; JP 58 183 611; U.S. Pat. No. 5,306,498; and U.S. Pat. No. 4,988,456.

U.S. Pat. Nos. 5,277,899 and 4,963,348, and WO 93/07848, disclose conditioners that have set retention properties. The disclosed compositions are oil-in-water emulsions (O/W), as opposed to the present $W_1/O$ primary emulsions and the $W_1$-O-$W_2$ multiple emulsion compositions.

Although various patents and publications disclose $W_1$-O-$W_2$ multiple emulsion compositions for cosmetic use, those compositions lack the stability needed for a consumer-acceptable topically-effective composition. The present invention therefore is directed to stable $W_1$-O-$W_2$ multiple emulsion compositions which are capable of depositing water-soluble, topically-active compounds onto hair or skin from compositions, such as hair conditioners, hair shampoos, or skin cleaners.

SUMMARY OF THE INVENTION

The present invention is directed to topically-effective $W_1$-O-$W_2$ multiple emulsion compositions having improved stability and efficacy, and to methods of using the $W_1$-O-$W_2$ multiple emulsion compositions. More particularly, the present invention is directed to a $W_1$-O-$W_2$ multiple emulsion composition comprising a continuous external aqueous phase ($W_2$) and a primary water-in-oil ($W_1$/O) emulsion as the dispersed internal phase. The primary $W_1$/O emulsion is emulsified in the external aqueous phase by a surfactant system that is capable of forming a layer of lamellar liquid crystals around droplets of the primary emulsion.

The primary $W_1$/O emulsion comprises a first topically-active compound, like a hair conditioner, a hair dye, a hair fixative, a skin care compound or a topical medicament; a surfactant phase comprising silicon-free surfactant or surfactant blend having an HLB value of about 10 or less, an oil-soluble silicon-based surfactant, an oil-soluble polymeric surfactant or a mixture thereof; an oil phase comprising a silicone compound or a hydrocarbon compound; and water. The external phase comprises water, a surfactant system capable of forming stabilizing liquid crystals, and preferably a second topically-active compound.

In particular, the $W_1$-O-$W_2$ multiple emulsion compositions comprise:

(a) about 40% to about 99% by weight of the composition of an external aqueous phase ($W_2$); and (b) about 1% to about 60% by weight of the composition of a primary $W_1$/O emulsion.

The primary $W_1$/O emulsion comprises:

(a) about 1% to about 95% by weight of the primary emulsion of an aqueous phase comprising (i) a first topically-active compound and (ii) water;

(b) about 0.5% to about 95% by weight of the primary emulsion of an oil phase comprising a volatile silicone compound, a nonvolatile silicone compound, a volatile hydrocarbon compound, a nonvolatile hydrocarbon compound, or a mixture thereof; and (c) about 0.1% to about 20% by weight of the primary emulsion of a surfactant phase comprising a silicon-free surfactant or surfactant blend having an HLB value of about 10 or less, an oil-soluble silicon-based surfactant, an oil-soluble polymeric surfactant, or a mixture thereof.

The external aqueous phase ($W_2$) includes a surfactant system capable of forming stabilizing liquid crystals as an emulsifier, and optionally includes a second topically-active compound which can perform the same or a different function from the first topically-active compound.

A $W_1$-O-$W_2$ multiple emulsion composition of the present invention can be a liquid composition having a viscosity of about 1 cps to about 15,000 cps (centipoise), and preferably about 100 to about 10,000 cps. To achieve the full advantage of the present invention, a liquid topically-effective composition has a viscosity of about 1,000 to about 9,000 cps. The $W_1$-O-$W_2$ multiple emulsion also can be cream-like and have a viscosity of about 50,000 to about 1,200,000 cps, and preferably about 100,000 to about 1,000,000 cps.

The $W_1$-O-$W_2$ multiple emulsion compositions of the present invention are: (1) leave-on compositions, which are designed for application to the skin or hair without a subsequent rinsing step or (2) rinse-off compositions, which are designed for application to the skin or hair, followed by rinsing from the skin or hair. For either type of composition, the second topically-active compound, if present in the external aqueous phase, performs its intended function during and after topical application of the composition to the skin or hair. If the composition is a rinse-off composition, the droplets of the primary $W_1$/O emulsion are of sufficient size, i.e., a range of about 5 to about 1000$\mu$ (microns), and preferably about 10 to about 500$\mu$, in diameter, to resist removal from the skin or hair during the rinsing step. The droplets of the internal $W_1$ phase of the $W_1$/O primary emulsion range in size from about 1 to about 75$\mu$.

For either a leave-on or a rinse-off composition, the external oil phase of the primary $W_1$/O emulsion then can evaporate during drying of the skin or hair to release the first topically-active compound present in the internal aqueous phase of the primary emulsion. Alternatively, the internal aqueous phase is released by rubbing the skin or hair to break the $W_1$/O primary emulsion. The first topically-active compound then can contact the skin or hair to perform its intended function. In another embodiment, the primary $W_1$/O emulsion is not broken, but is allowed to remain on the skin or hair as is. Typically, the first topically-active compound is not rinsed from the skin or hair.

In accordance with an important aspect of the present invention, a water-soluble (or water-dispersible), topically-active compound therefore can be incorporated into a rinse-off composition without wasting a substantial amount of the topically-active compound during the rinsing step.

Another important aspect of the present invention is the ability to treat the skin or hair with incompatible water-soluble, topically-active compounds using a single $W_1$-O-$W_2$ multiple emulsion composition. The composition can be a rinse-off or a leave-on product. By incorporating the first topically-active compound in the internal aqueous phase of the primary emulsion ($W_1$) and the second topically-active compound in the external aqueous phase of the composition ($W_2$), the oil phase (O) provides a barrier that separates the two incompatible topically-active compounds and precludes contact between the compounds. Incompatible topically-active compounds therefore can be applied to the hair or skin from a single composition, as opposed to applying the topically-active compounds individually from two different compositions.

For example, it is well known that an anionic compound, like an anionic dye, and a cationic compound, like a quaternary ammonium compound, are incompatible. However, these incompatible compounds can be included in the present $W_1$-O-$W_2$ multiple emulsion compositions.

The quaternary ammonium compound is present as the second topically-active compound in the external aqueous phase ($W_2$). Upon application to the hair, the quaternary ammonium compound is substantive to, and conditions, the hair. The primary $W_1$/O emulsion, which incorporates the anionic dye (i.e., the first topically-active compound) in the aqueous phase, also is present on the hair. The oil phase provides further conditioning benefits to the wet hair, and can evaporate during hair drying to release the anionic dye, which colors the hair. Similarly, an anionic compound can be the second topically-active compound to cleanse the hair and a cationic compound can be the first topically-active compound to condition the hair.

In accordance with another important aspect of the present invention, the first topically-active compound is water soluble or water dispersible. The first topically-active compound therefore can be rinsed from the skin or the hair during a subsequent shampooing or rinsing to preclude an undesirable residue of first topically-active compound building up on the hair.

In another embodiment of the present invention, the first and second topically-active compounds are compatible, yet perform different functions. For example, the second topically-active compound can be a cleansing compound for the skin or hair, and the first topically-active compound can be a topical medicament, a hair fixative, or a hair dye, for example.

In another important embodiment, the external aqueous phase does not include a second topically-active compound. In this embodiment, the first topically-active compound in the primary $W_1$/O emulsion is precluded from contacting the skin or hair until desired. For example, present day water-soluble hair dye compositions stain the hands of the applicator, sinks and countertops. The present $W_1$-O-$W_2$ multiple emulsion compositions allow application of a water-soluble dye to hair, wherein the dye is released only after the composition is applied to the hair, and the hair is dried. Staining of hands, sinks and countertops therefore is avoided. Composition economics also is enhanced because the water-soluble hair dye, a relatively expensive ingredient, is not rinsed from the hair and wasted.

In yet another important embodiment, a $W_1$-O-$W_2$ multiple emulsion composition of the present invention incorporates a skin cleansing agent or a skin conditioning agent as the second topically-active compound and an astringent salt as the first topically-active compound to form a stable and efficacious deodorant-cleanser composition. In other embodiments of the present invention, the first topically-active compound is a topically-effective drug or medicament; a topical anesthetic; a sunscreen agent; a skin care agent; a skin-soothing emollient or other topical cosmetic compound; a topical anti-inflammatory; and the like.

The first topically-active compound incorporated into the multiple emulsion compositions of the present invention preferably is water soluble and is incorporated into the aqueous phase of the primary $W_1$/O emulsion. As used herein, the term "water soluble" means "water soluble or water dispersible". However, water-insoluble topically-active compounds also can be incorporated into the oil phase of the primary $W_1$/O emulsion.

In a preferred embodiment, the $W_1$-O-$W_2$ multiple emulsion compositions comprise:
 (A) about 50% to about 95% by weight of the composition of an external aqueous phase, said external aqueous phase comprising:
  (i) about 0.1% to about 30% by weight of the external aqueous phase of a second topically-active compound;
  (ii) about 0.5% to about 10% by weight of the external aqueous phase of a surfactant system capable of forming stabilizing liquid crystals; and
  (iii) water;
 (B) about 5% to about 50% by weight of the composition of a primary water-in-oil emulsion, said primary emulsion comprising:
  (i) about 10% to about 95% by weight of the primary emulsion of an aqueous phase, said aqueous phase comprising (a) water and (b) a topically-effective amount of a first topically-active compound, typically about 0.1% to about 30% by weight based on the total weight of the primary emulsion;
  (ii) about 0.5% to about 80% by weight of the primary emulsion of an oil phase comprising a volatile silicone compound, a volatile compound, or a mixture thereof; and
  (iii) about 0.1% to about 15% by weight of the primary emulsion of a surfactant phase comprising a silicon-free surfactant or surfactant blend having an HLB value of about 1 to about 7, an oil-soluble silicon-based surfactant, an oil-soluble polymeric surfactant or a mixture thereof.

Other aspects of the present invention include providing a phase stable, topically-effective composition for the administration of one or more water-soluble, topically-active compounds to the skin or hair by providing a primary $W_1$/O emulsion having a droplet size of about 5 to about 1000µ.

The present $W_1$-O-$W_2$ multiple emulsion compositions are stable over extended storage periods, can be essentially nonstaining, effectively deliver one or more water-soluble, topically-active compounds to the skin and hair, and exhibit excellent esthetic and functional properties for consumer acceptance.

The above and other advantages and novel features of the present invention will become apparent from the following detailed description of the preferred embodiments.

DETAILED DESCRIPTION OF THE PREFERRED EMBODIMENTS

A topically-effective composition of the present invention is a stable, $W_1$-O-$W_2$ multiple emulsion comprising an external aqueous phase and an internal primary emulsion. The primary emulsion comprises a first water-soluble, topically-active compound, such as a hair conditioner, a hair fixative, a hair dye or a topical medicament; a surfactant phase comprising a silicon-free surfactant or surfactant blend having an HLB value of about 10 or less, an oil-soluble silicon-based surfactant, an oil-soluble polymeric surfactant, or a mixture thereof; an oil phase comprising a volatile silicone compound, a nonvolatile silicone compound, a volatile hydrocarbon compound, a nonvolatile hydrocarbon compound, or a mixture thereof; and water. The external phase comprises water and a surfactant system capable of forming liquid crystals.

The $W_1$-O-$W_2$ multiple emulsion composition can be a liquid having a viscosity in the range of about 1,000 to about 15,000 cps. The multiple emulsion composition also can be a cream having a viscosity of about 50,000 to about 1,200,000 cps.

After application to the skin or hair, the external aqueous phase can be rinsed from the skin or hair. Alternatively, a rinsing step can be omitted. In either embodiment, the oil phase of the primary emulsion, if sufficiently volatile, evaporates during the skin or hair drying process to release the internal aqueous phase of the primary emulsion, thereby allowing the first topically-active compound to contact the skin or hair and perform its intended function. If the oil phase is not volatile, the internal aqueous phase is released by rubbing the skin or hair to break the primary emulsion.

The water-in-oil-in-water multiple emulsion compositions of the present invention are designated herein as $W_1$-O-$W_2$ multiple emulsions. This designation indicates that an oil phase (O) separates an encapsulated, discontinuous aqueous phase ($W_1$) from a continuous aqueous phase ($W_2$). Conventionally, the $W_1$ and $W_2$ phases differ in compositional make-up, but the $W_1$ and $W_2$ phases can be identical.

In accordance with an important feature of the present invention, the liquid $W_1$-O-$W_2$ multiple emulsion compositions are stable compositions that effectively resist coalescence of primary $W_1$/O droplets over long storage periods. The $W_1$-O-$W_2$ compositions also resist leakage or transfer of water-soluble components between the aqueous internal phase of the primary emulsion ($W_1$) and the external aqueous phase ($W_2$). A $W_1$-O-$W_2$ multiple emulsion composition generally is available for immediate application to the skin or hair without the need to shake or agitate the composition in order to redisperse composition ingredients throughout the composition prior to use.

In particular, the $W_1$-O-$W_2$ multiple emulsion compositions comprise:

(a) about 40% to about 99% by weight of the composition of an external aqueous phase; and
(b) about 1% to about 60% by weight of the composition of a primary $W_1$/O emulsion.

The primary $W_1$/O emulsion comprises:

(a) about 1% to about 95% by weight of the primary emulsion of an aqueous phase comprising (i) water and (ii) a topically-effective amount of a first topically-active compound, typically about 0.1% to about 30% by weight of the primary emulsion;
(b) about 0.5% to about 95% by weight of the primary emulsion of an oil phase comprising a volatile silicone compound, a nonvolatile silicone compound, a volatile hydrocarbon compound, a nonvolatile hydrocarbon compound, or a mixture thereof; and
(c) about 0.1% to about 20% by weight of the primary emulsion of a surfactant phase comprising a silicon-free surfactant or surfactant blend having an HLB value of about 10 or less, and preferably about 7 or less, an oil-soluble silicon-based surfactant, an oil-soluble polymeric surfactant, or a mixture thereof.

The external aqueous phase ($W_2$) comprises: (a) 0.1% to about 15% based on the weight of the external aqueous phase of a surfactant system capable of forming stabilizing liquid crystals as an emulsifier, and optionally, (b) a topically-effective amount of a second topically-active compound, typically 0% to about 30% by weight of the external phase, to perform a function identical to, similar to or different from the first topically-active compound.

The $W_1$-O-$W_2$ multiple emulsion compositions are stable and exhibit exceptional esthetic and functional properties.

The $W_1$-O-$W_2$ multiple emulsion compositions are liquids or creams, and are capable of effectively delivering one or more topically-active compounds to the skin or hair from a single composition.

I. The Primary Water-in-Oil ($W_1$/O) Emulsion

The primary $W_1$/O emulsion comprises water, a first topically-active compound, an oil phase and a surfactant phase. The water and first topically-active compound comprise the aqueous phase of the primary $W_1$/O emulsion. The primary emulsion comprises droplets containing water and the first topically-active compound (i.e., the aqueous phase). The droplets containing water and the first topically-active compound ($W_1$) have a diameter ranging from about 1 to about 75$\mu$ and are enveloped by a membrane or film comprising the oil phase and the surfactant phase. The contents of the internal aqueous phase ($W_1$) therefore do not contact the external aqueous phase ($W_2$) of the $W_1$-O-$W_2$ multiple emulsion.

The primary $W_1$/O emulsion is present in a $W_1$-O-$W_2$ multiple emulsion composition in an amount of about 1% to about 60%, and preferably about 5% to about 50%, by weight of the multiple emulsion composition. To achieve the full advantage of the present invention, the primary $W_1$/O emulsion is present in an amount of about 10% to about 45%, by weight of the multiple emulsion composition.

A. The Aqueous Phase

The aqueous phase is the internal phase ($W_1$) of the primary $W_1$/O emulsion. The internal aqueous phase constitutes about 1% to about 95% by weight of the primary emulsion, and the relatively small amounts of oil phase and surfactant phase separate the internal aqueous phase ($W_1$) of the primary emulsion from the external aqueous phase ($W_2$).

The aqueous phase ($W_1$) of the present $W_1$-O-$W_2$ multiple emulsion compositions comprises water and a first topically-active compound. The aqueous phase can further comprise additional topically-active compounds and/or optional water-soluble compounds capable of providing a desired esthetic or functional effect, such as a fragrance.

The aqueous phase ($W_1$) comprises about 1% to about 95%, and preferably about 10% to about 95%, by weight of the primary emulsion. To achieve the full advantage of the present invention, the aqueous phase comprises about 25% to about 95% by weight of the primary emulsion. Alternatively expressed, the internal aqueous $W_1$ phase is present in an amount of about 0.01% to about 57%, preferably about 0.5% to about 47.5%, and most preferably about 2.5% to about 42.75%, by weight of the $W_1$-O-$W_2$ multiple emulsion composition.

1. Topically-Active Compounds

In accordance with an important feature of the present invention, a wide variety of topically-active compounds can be incorporated into the aqueous phase of the primary $W_1$/O emulsion as the first topically-active compound. The topically-active compounds are water-soluble or water-dispersible and include both cosmetic and medicinal compounds that act upon contact with the skin or hair. The first topically-active compound is present in a sufficient amount to perform its intended function, typically in an amount of about 0.1% to about 30% by weight of the primary emulsion, or, alternatively expressed, about 0.001% to about 17.1% by weight of the $W_1$-O-$W_2$ multiple emulsion composition.

The first topically-active compound typically remains on the skin or hair after application, as opposed to being rinsed from the skin or hair. However, particular first topically-active compounds are designed to be rinsed from the skin or hair after the compound performs its intended function.

In accordance with an important feature of the present invention, the first topically-active compound can be incorporated into the aqueous phase or into the oil phase of the primary emulsion. Whether a particular first topically-active compound is incorporated into the aqueous phase or the oil phase of the primary emulsion is related to the solubility of the topically-active composition in water. In preferred embodiments, the first topically-active compound is water soluble and is incorporated into the internal $W_1$ aqueous phase.

As used herein, the term "water soluble" means water soluble or water dispersible. A water-soluble compound has a water solubility of at least 0.1 g (grams) per 100 ml (milliliters) of water and forms a true solution. A water-soluble compound can be inherently water soluble or can be made water soluble by the addition of a solubilizing compound, such as a coupling agent, a co-surfactant, or a solvent. A water-dispersible compound remains dispersed in water for at least the time period necessary to manufacture the primary $W_1$/O emulsion, i.e., at least about one hour.

In addition, the first topically-active compound can be incorporated into the aqueous phase and another topically-active compound can be incorporated into the oil phase to achieve enhanced efficacy (e.g., the primary emulsion includes a medicament in each of the aqueous and oil phases) or to provide different benefits (e.g., the primary emulsion includes a medicament in the aqueous phase and a topical anesthetic in the oil phase).

The first topically-active compound therefore can be one of, or a combination of, a cosmetic compound, a medicinally-active compound or any other compound that is useful upon topical application to the skin or hair. Such topically-active compounds include, but are not limited to, hair and skin conditioners, hair and skin cleansers, hair fixatives, hair dyes, hair growth promoters, deodorants, skin care compounds, permanent wave compounds, hair relaxers, hair straighteners, antibacterial compounds, antifungal compounds, anti-inflammatory compounds, topical anesthetics, sunscreens and other cosmetic and medicinal topically-effective compounds.

In accordance with an important feature of the present invention, the first topically-active compound comprises a water-soluble hair conditioner, such as a quaternary ammonium compound. Quaternary ammonium compounds are substantive to the hair and are excellent hair conditioners, but have a well-known incompatibility with anionic surfactants and anionic dyes. Therefore, quaternary ammonium compounds generally are not a component in shampoo-conditioner compositions or anionic dye-based compositions, but are applied to the hair from a separate conditioning composition.

The water-soluble quaternary ammonium compounds have the general structural formula:

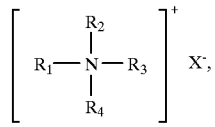

wherein $R_1$ is an alkyl group including from about 8 to about 18 carbon atoms; $R_2$ is selected from the group consisting of an alkyl group including from about 8 to about 18 carbon atoms, a hydrogen atom, a methyl group, an ethyl group, a hydroxymethyl group and a hydroxyethyl group; $R_3$ is selected from the group consisting of a benzyl group, a hydrogen atom, a methyl group, an ethyl group, a hydroxymethyl group and a hydroxyethyl group; $R_4$ is selected from the group consisting of a hydrogen atom, a methyl group, an ethyl group, a hydroxymethyl group and a hydroxyethyl group; and X is an anion. The quaternary nitrogen of the water-soluble quaternary ammonium compound also can be a component of a heterocyclic nitrogen-containing moiety, such as morpholine or pyridine. The anion of the quaternary ammonium compound can be any common anion, such as chloride, methosulfate, ethosulfate, nitrate, bromide, tosylate, acetate, or phosphate.

The water-soluble quaternary ammonium compounds have one or two long chain alkyl groups containing from about 8 to about 18 carbon atoms. The long chain alkyl groups also can include, in addition to, or in replacement of, carbon and hydrogen atoms, ether linkages or similar water-solubilizing linkages. The remaining two or three substituents of the quaternary nitrogen of the quaternary ammonium compound can be hydrogen; or benzyl; or short chain alkyl or hydroxyalkyl groups, such as methyl, ethyl, hydroxymethyl or hydroxyethyl groups; or combinations thereof, either of the same or different identity.

Exemplary water-soluble quaternary ammonium compounds include, but are not limited to, laurtrimonium chloride; Quaternium-16; lauralkonium chloride; olealkonium chloride; dilauryldimonium chloride; cetalkonium chloride; dicetyldimonium chloride; laurylpyridinium chloride; cetylpyridinium chloride; soyatrimonium chloride; Polyquaternium-6; Polyquaternium-7; guarhydroxypropyltrimonium chloride; Polyquaternium11; Polyquaternium-5; Polyquaternium-10; Polyquaternium-24; cetrimonium chloride; Quaternium-24; mytrimonium chloride; PEG-2 cocomonium chloride; PEG-2 cocoyl quaternium-4; PEG-15 cocoyl quaternium-4; PEG-2 stearyl quaternium-4; PEG-15 stearyl quaternium-4; PEG-2 oleyl quaternium-4; and PEG-15 oleyl quaternium-4, and mixtures thereof, wherein the compound designation is provided by the Cosmetic, Toiletry and Fragrance Association, Inc. in the *CTFA Cosmetic Ingredient Dictionary*, 4th Ed., 1991, hereinafter referred to as the *CTFA Dictionary*. Other water-soluble quaternary ammonium compounds are listed in the *CTFA Cosmetic Ingredient Handbook*, 1st Ed., 1988 (hereinafter the *CTFA Handbook*) at pages 40–42, incorporated herein by reference.

Other water-soluble hair conditioners also can be used as the first topically-active compound. Such hair conditioners include, but are not limited to, fatty amine salts, ethoxylated fatty amine salts, dimethicone copolyols, protonated polyethylenimines, protonated ethoxylated polyethylenimines, soluble animal collagen, lauramine oxide, cationic polymers, numerous other water-soluble hair conditioners listed in the *CTFA Handbook* at pages 71–73, incorporated herein by reference, and mixtures thereof.

In addition to hair conditioners, a skin conditioner can be used as the first topically-active compound. Skin conditioning agents include, but are not limited to, humectants, such as fructose, glucose, glycerin, propylene glycol, glycereth-26, mannitol and urea; pyrrolidone carboxylic acid; hydrolyzed lecithin; coco-betaine; cysteine hydrochloride; glutamine; PPG-15; sodium gluconate; potassium aspartate; oleyl betaine; thiamine hydrochloride; sodium laureth sulfate; sodium hyaluronate; hydrolyzed proteins; hydrolyzed keratin; amino acids; amine oxides; water-soluble derivatives of vitamins A, E and D; amino-functional silicones; ethoxylated glycerin; alpha-hydroxy acids and salts thereof; water-soluble fatty oil derivatives, such as PEG-24 hydrogenated lanolin, almond oil, grape seed oil and castor oil; numerous other water-soluble skin conditioners listed in the *CTFA Handbook*, pages 79–84, incorporated herein by reference; and mixtures thereof.

The first topically-active compound also can be a hair fixative or film former that imparts style-retention properties to hair, i.e., sets the hair. The hair fixative typically is a homopolymer, a copolymer, or a terpolymer. The polymers can be nonionic, amphoteric, anionic or cationic. Examples of hair fixatives include, but are not limited to, an acrylamide copolymer; an acrylamide/sodium acrylate copolymer; a polystyrene sulfonate; a polyethylene oxide; a water-dispersible polyester; a cationic cellulose; an acrylate/ammonium methacrylate copolymer; an aminoethylacrylate phosphate/acrylate copolymer; a polyacrylamide; Polyquaternium-1; Polyquaternium-2; Polyquaternium-4; Polyquaternium-5; Polyquaternium-6; Polyquaternium-7; Polyquaternium-8; Polyquaternium-9; Polyquaternium-10; Polyquaternium-11; Polyquaternium-12; Polyquaternium-13; Polyquaternium-14; Polyquaternium-15; Polyquaternium-16; Polyquaternium-28; a PVP (polyvinylpyrrolidone); a PVP/dimethylaminoethylmethacrylate copolymer; a PVP/ethyl methacrylate/methacrylic acid copolymer; a carboxylated polyvinyl acetate; vinyl/caprolactam/PVP/dimethylaminoethyl methacrylate copolymer (GAFFIX VC713); a PVP/vinyl acetate copolymer; a sodium acrylate/vinyl alcohol copolymer; sodium carrageenan; a vinyl acetate/crotonic acid copolymer; numerous other water-soluble hair fixatives listed in the *CTFA Handbook* at pages 73–74, incorporated herein by reference; and mixtures thereof. Numerous hair fixatives also are disclosed in U.S. Pat. No. 5,277,899, incorporated herein by reference.

In addition, the first topically-active compound can be a water-soluble hair dye, such as, but not limited to, m-aminophenol hydrochloride, p-aminophenol sulfate, 2,3-diaminophenol hydrochloride, 1,5-naphthalenediol, p-phenylenediamine hydrochloride, sodium picramate, water-soluble cationic dyes, water-soluble anionic dyes, water-soluble FD&C dyes, like Blue No. 1, Blue No. 2, Red No. 3, Red No. 4, or Red No. 40, water-soluble D&C dyes, like Yellow No. 10, Red No. 22 or Red No. 28, and pyrogallol. Numerous other hair dyes are listed in the *CTFA Handbook*, pages 70–71, incorporated herein by reference.

The first topically-active compound also can be an antioxidant, like ascorbic acid or erythorbic acid; or a fluorescent whitening agent or optical brightener, like a distyrylbiphenyl derivative, stilbene or a stilbene derivative, a pyralozine derivative or a coumarin derivative. In addition, a self-tanning compound, like dihydroxy acetone, or a hair growth promoter, or a hair bleaching agent, like a perborate or a persulfate salt, can be the first topically-active compound.

The first topically-active compound also can be a deodorant compound, such as an astringent salt or a bioactive compound. The astringent salts include organic and inorganic salts of aluminum, zirconium, zinc, and mixtures thereof. The anion of the astringent salt can be, for example, sulfate, chloride, chlorohydroxide, alum, formate, lactate, benzyl sulfonate or phenyl sulfonate. Exemplary classes of antiperspirant astringent salts include aluminum halides, aluminum hydroxyhalides, zirconyl oxyhalides, zirconyl hydroxyhalides, and mixtures thereof.

Exemplary aluminum salts include aluminum chloride and the aluminum hydroxyhalides having the general formula $Al_2(OH)_xQ_y \cdot XH_2O$, wherein Q is chlorine, bromine or iodine; x is about 2 to about 5; x+y is about 6, wherein x and y are not necessarily integers; and X is about 1 to about 6. Exemplary zirconium compounds include zirconium oxy salts and zirconium hydroxy salts, also referred to as zirconyl salts and zirconyl hydroxy salts, and represented by the general empirical formula $ZrO(OH)_{2-nz}L_z$, wherein z varies from about 0.9 to about 2 and is not necessarily an integer; n is the valence of L; 2–nz is greater than or equal to 0; and L is selected from the group consisting of halides, nitrate, sulfamate, sulfate, and mixtures thereof.

Exemplary deodorant compounds therefore include, but are not limited to, aluminum bromohydrate, potassium alum, sodium aluminum chlorohydroxy lactate, aluminum sulfate, aluminum chlorohydrate, aluminum-zirconium tetrachlorohydrate, an aluminum-zirconium polychlorohydrate complexed with glycine, aluminum-zirconium trichlorohydrate, aluminum-zirconium octachlorohydrate, aluminum sesquichlorohydrate, aluminum sesquichlorohydrex PG, aluminum chlorohydrex PEG, aluminum zirconium octachlorohydrex glycine complex, aluminum zirconium pentachlorohydrex glycine complex, aluminum zirconium tetrachlorohydrex glycine complex, aluminum zirconium trichlorohydrex glycine complex, aluminum chlorohydrex PG, zirconium chlorohydrate, aluminum dichlorohydrate, aluminum dichlorohydrex PEG, aluminum dichlorohydrex PG, aluminum sesquichlorohydrex PG, aluminum chloride, aluminum zirconium pentachlorohydrate, numerous other useful antiperspirant compounds listed in the *CTFA Handbook* at p. 56, incorporated herein by reference, and mixtures thereof.

In addition to the astringent salts, the deodorant compound can be a bacteriostatic quaternary ammonium compound, such as, for example, cetyl trimethyl ammonium bromide, cetyl pyridinium chloride, benzethonium chloride, diisobutylbenzoxyethoxyethyl-dimethylbenzyl ammonium chloride, sodium N-lauryl sarcosine, sodium N-polymethyl sarcosine, lauroyl sarcosine, N-myristolyl glycine, potassium N-lauroyl sarcosine, and stearyl trimethyl ammonium chloride; or a bioactive compound; or a carbonate or bicarbonate salt, such as, for example, the alkali metal carbonates and bicarbonates, and the ammonium and tetralkylammonium carbonates and bicarbonates.

In addition, other compounds can be included in the primary emulsion as the first topically-active compound in an amount sufficient to perform their intended function. For example, if the composition is intended to be a sunscreen, then compounds such as benzophenone-4, trihydroxycinnamic acid and salts, tannic acid, uric acid, quinine salts, dihydroxy naphtholic acid; an anthranilate, diethanolamine methoxycinnamate, p-aminobenzoic acid, phenylbenzimidazole sulfonic acid, PEG-25 p-aminobenzoic acid or triethanolamine salicylate can be incorporated into the internal aqueous $W_1$ phase.

Further, sunscreen compounds such as dioxybenzone, ethyl 4-[bis(hydroxypropyl)] aminobenzoate, glyceryl aminobenzoate, homosalate, menthyl anthranilate, octocrylene, octyl methoxycinnamate, octyl salicylate, oxybenzone, padimate O, red petrolatum, titanium dioxide, 4-menthylbenzylidene camphor, benzophenone-1, benzophenone-2, benzophenone-6, benzophenone-12, isopropyl dibenzoyl methane, butyl methoxydibenzoylmethane, zotocrylene, or zinc oxide can be incorporated into the organic phase of the primary emulsion. Other sunscreen compounds soluble in either the aqueous or organic phase are listed in *CTFA Handbook*, pages 86 and 87, incorporated herein by reference.

Similarly, topically-active drugs, like antifungal compounds; antibacterial compounds; anti-inflammatory compounds; topical anesthetics; skin rash, skin disease and dermatitis medications; and anti-itch and irritation-reducing compounds can be included in the compositions of the present invention. For example, analgesics such as benzocaine, dyclonine hydrochloride, aloe vera and the like;

anesthetics such as butamben picrate, lidocaine hydrochloride, xylocaine and the like; antibacterials and antiseptics, such as povidone-iodine, polymyxin b sulfate-bacitracin, zinc-neomycin sulfate-hydrocortisone, chloramphenicol, methylbenzethonium chloride, and erythromycin and the like; antiparasitics, such as lindane; deodorants, such as chlorophyllin copper complex, aluminum chloride, aluminum chloride hexahydrate, and methylbenzethonium chloride; essentially all dermatologicals, like acne preparations, such as benzoyl peroxide, erythromycin-benzoyl peroxide, clindamycin phosphate, 5,7-dichloro-8-hydroxyquinoline, and the like; anti-inflammatory agents, such as alclometasone dipropionate, betamethasone valerate, and the like; burn relief ointments, such as o-amino-p-toluenesulfonamide monoacetate and the like; depigmenting agents, such as monobenzone; dermatitis relief agents, such as the active steroid amcinonide, diflorasone diacetate, hydrocortisone, and the like; diaper rash relief agents, such as methylbenzethonium chloride and the like; emollients and moisturizers, such as mineral oil, PEG-4 dilaurate, lanolin oil, petrolatum, mineral wax and the like; fungicides, such as butocouazole nitrate, haloprogin, clotrimazole, and the like; herpes treatment drugs, such as O-[(2-hydroxyethoxy)methyl]guanine; pruritic medications, such as alclometasone dipropionate, betamethasone valerate, isopropyl myristate MSD, and the like; psoriasis, seborrhea and scabicide agents, such as anthralin, methoxsalen, coal tar and the like; steroids, such as 2-(acetyloxy)-9-fluoro-1',2',3',4'-tetrahydro-11-hydroxypregna-1,4-dieno[16,17-b]naphthalene-3,20-dione and 21-chloro-9-fluoro-1',2',3',4'-tetrahydro-11b-hydroxypregna-1,4-dieno[16z,17-b]naphthalene-3,20-dione. Any other medication capable of topical administration also can be incorporated in a composition of the present invention in an amount sufficient to perform its intended function. Other topically-active compounds are listed in *Remington's Pharmaceutical Sciences*, 17th Ed., Merck Publishing Co., Easton, Pa. (1985), pages 773–791 and pages 1054–1058 (hereinafter *Remington's*), incorporated herein by reference.

An above-described first topically-active compound is designed to remain on the skin or hair to perform its intended function. However, in particular situations, a first topically-active compound that is rinsed from the skin or hair can be incorporated into the internal aqueous $W_1$ phase of the primary emulsion.

For example, a $W_1$-O-$W_2$ multiple emulsion composition designed as a permanent wave composition can incorporate a reducing agent into the external aqueous phase as the second topically-active compound. After applying the $W_1$-O-$W_2$ composition to the hair and allowing the composition to contact the hair for a sufficient time to reduce the hair, the external aqueous phase is rinsed from the hair leaving droplets of the primary emulsion on the hair.

The primary emulsion has incorporated therein an oxidizing agent as the first topically-active compound. After the oil phase, and preferably a volatile oil phase, evaporates from the primary emulsion, the oxidizing agent is released to neutralize the hair and any reducing agent remaining on the hair. Excess oxidizing agent then can be rinsed from the hair in a second rinsing step.

Exemplary, but non-limiting, oxidizing agents used as the first topically-active compound are ammonium persulfate, hydrogen peroxide, potassium bromate, potassium chromate, potassium persulfate, sodium bromate, sodium carbonate peroxide, sodium iodate, sodium perborate, sodium persulfate, urea peroxide, and mixtures thereof. An oxidizing agent also can be the second topically-active compound when the first topically-active compound is a hair conditioner. In addition, the second topically-active compound can be a bleaching agent (i.e., an oxidizing agent) and the first topically-active compound can be a hair dye.

2. Water

Sufficient water is present in the aqueous phase such that the aqueous phase comprises about 1% to about 95% by weight of the primary emulsion. Total water present in the $W_1$-O-$W_2$ multiple emulsion composition is about 30% to about 99.9%, and typically about 40% to about 95%, by weight of the composition.

3. Optional Ingredients

The internal aqueous phase also can include optional ingredients traditionally included in topically-applied compositions. These optional ingredients include, but are not limited to, dyes, fragrances, preservatives, antioxidants, detackifying agents, and similar types of compounds. The optional ingredients are included in the internal aqueous phase of the primary emulsion in an amount sufficient to perform their intended function.

B. The Oil Phase

The primary $W_1$/O emulsion also comprises about 0.5% to about 95%, preferably about 0.5% to about 80%, and most preferably about 0.5% to about 75%, by weight of the primary emulsion of an oil phase; alternatively expressed as about 0.005% to about 57%, preferably about 0.005% to about 48%, and most preferably about 0.005% to about 45%, by weight of the $W_1$-O-$W_2$ multiple emulsion composition. The oil phase encapsulates the internal aqueous $W_1$ phase of the primary emulsion to form droplets of about 5 to about 1,000$\mu$, and preferably about 10 to about 500$\mu$, in diameter. The oil phase therefore provides a barrier between the internal aqueous phase of the primary emulsion and the external aqueous phase of the $W_1$-O-$W_2$ multiple emulsion composition. The oil phase provides a sufficient barrier even though the oil phase constitutes as little as 0.5% by weight of the primary emulsion.

The oil phase can be a volatile oil phase, a nonvolatile oil phase, or a mixture thereof. A volatile oil phase comprising a volatile silicone compound, a volatile hydrocarbon compound, or a mixture thereof is preferred. In the preferred embodiment, the oil phase is sufficiently volatile to evaporate during the process of drying the skin or hair, and thereby release the internal aqueous $W_1$ phase, which includes the first topically-active compound, to contact the skin or hair.

A nonvolatile oil phase, comprising a nonvolatile silicone compound, a nonvolatile hydrocarbon compound, or a mixture thereof, remains on the skin or hair. In this embodiment, the first topically-active compound is released by rubbing the skin or hair to break the primary $W_1$/O emulsion.

In accordance with an important feature of the present invention, the oil phase comprises a combination of a volatile oil phase and a nonvolatile oil phase. In this embodiment, an oil phase can be designed to evaporate at a preselected temperature and provide a controlled release of the first topically-active compound at the preselected temperature. Preselected temperatures are those encountered during normal hair drying, provided by a hair dryer, or provided by a curling iron.

As previously stated, the oil phase also can include a water-insoluble topically-active compound in a sufficient amount to impart a particular functional or esthetic effect (e.g., emolliency), as long as the topically-active compound does not adversely affect the $W_1$-O-$W_2$ multiple emulsion composition (e.g., does not impart emulsion instability). Although the oil phase can incorporate a topically-active compound, the topically-active compound preferably is incorporated into the internal aqueous phase.

The oil phase can comprise a volatile oil phase, a nonvolatile oil phase or a mixture thereof. The volatile oil phase comprises a volatile silicone compound, a volatile hydrocarbon compound or a mixture thereof. Preferably, the volatile oil phase comprises a volatile silicone compound. The volatile oil phase evaporates from the skin or hair to release the first topically-active compound.

Exemplary volatile compounds include, but are not limited to, volatile, low molecular weight polydimethylsiloxane compounds. The volatile, low molecular weight polydimethylsiloxane compound can be either a linear or a cyclic polydimethylsiloxane compound, as long as the polydimethylsiloxane compound has sufficient volatility to volatilize after topical application to the skin or hair. Preferably the polydimethylsiloxane is a cyclic siloxane, like cyclomethicone. The volatile silicone evaporates relatively quickly to leave only the nonvolatile components of the primary emulsion on the skin. In general, volatile polydimethylsiloxane compounds useful in the compositions of the present invention include polydimethylsiloxane compounds having a viscosity of about 0.5 to about 10 cs (centistokes). The preferred volatile polydimethylsiloxanes have a viscosity in the range of about 0.5 to about 6 cs.

The cyclic, low molecular weight, volatile polydimethylsiloxanes, designated in the *CTFA International Cosmetic Ingredient Dictionary*, 4th Ed., Cosmetic, Toiletry and Fragrance Association, Washington, D.C. (1991) (hereinafter *CTFA Dictionary*) as cyclomethicones, are the preferred siloxanes used in a composition of the present invention. To achieve the full advantage of the present invention, a cyclomethicone used in a composition of the present invention is a low viscosity, low molecular weight, water-insoluble cyclic compound having an average of about 3 to about 6-[O—Si(CH$_3$)$_2$]- repeating group units per molecule (hexamethylcyclotrisiloxane, octamethylcyclotetrasiloxane, decamethylcyclopentasiloxane, dodecamethylcylcohexasiloxane, and mixtures thereof); boil at atmospheric pressure at about 150° C. to about 250° C.; and have a viscosity at 25° C. of about 2 to about 6 centistokes. The polydimethyl cyclosiloxanes having an average of about 4 to about 5 repeating units per molecule, i.e., the tetramer and pentamer, are especially preferred. To achieve the full advantage of the present invention, the volatile cyclomethicone has a boiling point at atmospheric pressure in the range of about 150° C. to about 220° C. Suitable cyclomethicones are available commercially under the tradenames DOW CORNING 245 FLUID, DOW CORNING 344 FLUID and DOW CORNING 345 FLUID from Dow Corning Corporation, Midland, Mich., and SILICONE SF-1173 and SILICONE SF-1202 from General Electric, Waterford, N.Y.

An example of a linear, low molecular weight, volatile polydimethylsiloxane compound useful in the composition and method of the present invention is the compound designated in the *CTFA Dictionary* as hexamethyldisiloxane, available commercially under the tradename DOW CORNING 200 FLUID from Dow Corning Corp., Midland, Mich. Hexamethyldisiloxane has a viscosity of 0.65 cs and is highly volatile. Other linear polydimethylsiloxanes, such as decamethyltetrasiloxane, having a boiling point of about 195° and a viscosity of 1.5 cs; octamethyltrisiloxane; and dodecamethylpentasiloxane, also have sufficient volatility to be useful in the composition of the present invention. Another useful linear siloxane is bisphenylhexamethicone. In general, it has been found that a linear, low molecular weight volatile polydimethylsiloxane compound having a viscosity at 25° C. and atmospheric pressure of about 0.5 to about 5 cs, and a boiling point at atmospheric pressure of about 100° C. to about 250° C., is preferred for use in the composition and method of the present invention.

The volatile oil phase also can comprise a volatile hydrocarbon compound, such as a hydrocarbon having about 10 to about 30 carbon atoms, that has sufficient volatility to slowly volatilize from the skin or hair after application of the $W_1$-O-$W_2$ multiple emulsion composition to the skin or hair and subsequent rinsing. A preferred volatile hydrocarbon compound is an aliphatic hydrocarbon having about 12 to about 24 carbon atoms, and having a boiling point of about 100° C. to about 250° C. The volatile hydrocarbon compounds perform the same function and provide essentially the same benefits as the volatile silicone compounds.

Volatile hydrocarbon compounds incorporated into the primary emulsion include, for example, isododecane and isohexadecane, i.e., PERMETHYL 99A, PERMETHYL 101A and PERMETHYL 102A, available from Presperse, Inc., South Plainfield, N.J. Other exemplary volatile hydrocarbon compounds are depicted in general structural formula (I), wherein n ranges from 2 to 5.

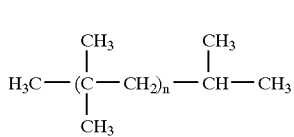

(I)

Another exemplary volatile hydrocarbon compound is ISOPAR M (a $C_{13}$–$C_{14}$ isoparaffin available from Exxon Chemical Co., Baytown, Tex.).

As previously stated, the oil phase also can be a nonvolatile oil phase. The nonvolatile oil phase comprises a nonvolatile silicone compound, a nonvolatile hydrocarbon, or a mixture thereof. Preferably, the nonvolatile oil phase comprises a nonvolatile silicone compound. The nonvolatile oil phase does not evaporate from the skin or hair. The first topically-active compound therefore is released by rubbing the skin or hair to rupture the primary $W_1$/O emulsion. A nonvolatile oil phase has a boiling point at atmospheric pressure of greater than about 250° C.

Exemplary nonvolatile silicone compounds include a polyalkyl siloxane, a polyaryl siloxane or a polyalkylaryl siloxane. Mixtures of these nonvolatile silicone compounds also are useful. The nonvolatile silicones are nonfunctional siloxanes or siloxane mixtures having a viscosity of about 10 to about 600,000 cs, and typically about 350 to about 10,000 cs, at 25° C. The so-called "rigid silicones", as described in U.S. Pat. No. 4,902,499, herein incorporated by reference, having a viscosity above 600,000 cs at 20° C., and a weight average molecular weight of at least about 500,000, also are useful in a composition of the present invention. A phenyltrimethicone also is useful as a nonvolatile silicone compound.

The preferred nonvolatile silicone compound is a nonvolatile polydimethylsiloxane compound, such as a mixture, in about a 2:1 weight ratio, of a low molecular weight polydimethylsiloxane fluid and a higher molecular weight polydimethylsiloxane gum. Preferred silicone gums include linear and branched polydimethylsiloxanes of the following general formula:

wherein n is a number from about 2,000 to about 15,000, and preferably from about 2,000 to about 7,000. Silicone gums useful in compositions of the present invention are available from a variety of commercial sources, including General Electric Company, Waterford, N.Y. and Dow Corning Corp., Midland, Mich.

The nonvolatile oil phase also can comprise a nonvolatile hydrocarbon compound, such as mineral oil. Other exemplary nonvolatile hydrocarbon compounds that can be incorporated into the oil phase include, but are not limited to, a branched 1-decene oligomer, like 1-decene dimer or a polydecene.

The oil phase also optionally can comprise (1) an oil, such as jojoba oil, wheat germ oil or purcellin oil; or (2) a water-insoluble emollient, such as, for example, an ester having at least about 10 carbon atoms, and preferably about 10 to about 32 carbon atoms.

Suitable esters include those comprising an aliphatic alcohol having about eight to about twenty carbon atoms and an aliphatic or aromatic carboxylic acid including from two to about twelve carbon atoms, or conversely, an aliphatic alcohol having two to about twelve carbon atoms with an aliphatic or aromatic carboxylic acid including about eight to about twenty carbon atoms. The ester is either straight-chained or branched. Preferably, the ester has a molecular weight of less than about 500. Suitable esters therefore include, for example, but are not limited to:

(a) aliphatic monohydric alcohol esters, including but not limited to:
   myristyl propionate,
   isopropyl isostearate,
   isopropyl myristate,
   isopropyl palmitate,
   cetyl acetate,
   cetyl propionate,
   cetyl stearate,
   isodecyl neopentanoate,
   cetyl octanoate,
   isocetyl stearate;
(b) aliphatic di- and tri-esters of polycarboxylic acids, including but not limited to:
   diisopropyl adipate,
   diisostearyl fumarate,
   dioctyl adipate, and
   triisostearyl citrate;
(c) aliphatic polyhydric alcohol esters, including but not limited to:
   propylene glycol dipelargonate;
(d) aliphatic esters of aromatic acids, including but not limited to:
   $C_{12}$–$C_{15}$ alcohol esters of benzoic acid,
   octyl salicylate,
   sucrose benzoate, and
   dioctyl phthalate.

Numerous other esters are listed in the *CTFA Handbook*, at pages 24 through 26, incorporated herein by reference.

C. The Surfactant Phase

The primary emulsion of the present invention also includes about 0.1% to about 20%, and preferably about 0.1% to about 15%, by weight of the primary emulsion of a surfactant phase. To achieve the full advantage of the present invention, about 0.5% to about 12% by weight of the surfactant phase is present in the primary emulsion. Alternatively expressed, the surfactant phase is present in an amount of about 0.001% to about 12%, preferably about 0.005% to about 7.5%, and most preferably about 0.05% to about 5.4%, by weight of the $W_1$-O-$W_2$ multiple emulsion composition.

The surfactant phase comprises a silicon-free surfactant, or a blend of silicon-free surfactants, having an HLB value of about 10 or less (i.e., an HLB value of about 0.1 to about 10), an oil-soluble silicon-based surfactant, an oil-soluble polymeric surfactant, or mixtures thereof. Preferably, the silicon-free surfactant or surfactant blend has an HLB value of about 1 to about 7. To achieve the full advantage of the present invention, the silicon-free surfactant or surfactant blend has an HLB value of about 3 to about 6. The term "oil-soluble" as used herein means a compound having a solubility of at least 0.1 g per 100 ml of oil phase to form a true solution.

The surfactant phase therefore comprises a single silicon-free surfactant having an HLB value of about 0.1 to about 10, or a blend of silicon-free surfactants having different HLB values such that the blend has an HLB value of about 1 to about 10. The surfactant phase also can comprise a blend of an oil-soluble silicon-based surfactant, or an oil-soluble polymeric surfactant, and a silicon-free surfactant or surfactant blend having an HLB value of about 10 or less. The above-described surfactant phases provide a water-in-oil emulsion.

Preferably, the surfactant phase comprises an oil-soluble silicon-based surfactant when the oil phase comprises a volatile or a nonvolatile silicone compound. If the oil phase is a volatile or nonvolatile hydrocarbon compound, the surfactant phase preferably comprises a silicon-free non-ionic surfactant or an oil-soluble polymeric surfactant. If a combination of a silicone compound and hydrocarbon compound is used as the oil phase, the surfactant phase preferably comprises a combination of (1) a silicon-based surfactant and (2) an oil-soluble silicon-free surfactant, an oil-soluble polymeric surfactant or a mixture thereof.

A silicon-free nonionic surfactant having an HLB value of about 0.1 to about 10 can be used alone as the surfactant phase of the present invention. The surfactant phase also can comprise a blend of silicon-free surfactants each having an HLB value of less than 10. In addition, silicon-free surfactants having an HLB value of about 0.1 to about 10 also can be used as the first surfactant of a surfactant blend having an HLB value of about 1 to about 10, then a silicon-free surfactant having an HLB of greater than about 10 is the second surfactant of the surfactant blend having an HLB of about 1 to about 10.

Typically, silicon-free nonionic surfactants having an HLB value of about 10 or less have a hydrophobic moiety, such as a long chain ($C_8$–$C_{22}$) alkyl group or an alkylated aryl group, and a hydrophilic chain comprising a small number (i.e., one to about six) of ethoxy moieties or a combination of ethoxy and propoxy moieties. The silicon-free nonionic surfactants having an HLB of greater than about 10 typically have the same type of hydrophobic moiety as the low HLB surfactants, but include more ethoxy and/or propoxy moieties.

The HLB value of a particular silicon-free surfactant can be found in *McCutcheon's Emulsifiers and Detergents, North American and International Editions*, MC Publishing Co., Glen Rock, N.J. (1993) (hereinafter *McCutcheon's*). Alternatively, the HLB value of a particular surfactant can be estimated by dividing the weight percent of oxyethylene in the surfactant by five (for surfactants including only ethoxy moieties). In addition, the HLB value of a surfactant blend can be estimated by the following formula:

$$HLB = (wt.\% \ A)(HLB_A) + (wt.\% \ B)(HLB_B),$$

wherein wt. % A and wt. % B are the weight percent of surfactants A and B in the silicon-free surfactant blend, and $HLB_A$ and $HLB_B$ are the HLB values for surfactants A and B, respectively.

Exemplary classes of silicon-free nonionic surfactants include, but are not limited to, polyoxyethylene ethers of fatty ($C_6$–$C_{22}$) alcohols, polyoxyethylene/polyoxypropylene ethers of fatty ($C_6$–$C_{22}$) alcohols, ethoxylated alkylphenols, polyethylene glycol ethers of methyl glucose, polyethylene glycol ethers of sorbitol, and mixtures thereof.

Exemplary silicon-free nonionic surfactants are the ethoxylated alcohols having an HLB value of about 0.1 to about 10. An especially preferred ethoxylated alcohol is laureth-1, i.e., lauryl alcohol ethoxylated with an average of one mole of ethylene oxide. Other suitable ethoxylated alcohols include laureth-2, laureth-3 and laureth-4. Numerous other nonionic surfactants having an HLB of about 0.1 to about 10 are listed in McCutcheon's at pages 229–236, incorporated herein by reference. Other exemplary silicon-free nonionic surfactants having an HLB value of about 0.1 to about 10 include, but are not limited to, the ethoxylated nonylphenols, ethoxylated octylphenols, ethoxylated dodecylphenols, ethoxylated fatty ($C_6$–$C_{22}$) alcohols having four or fewer ethylene oxide moieties, oleth-2, steareth-3, steareth-2, ceteth-2, oleth-3, and mixtures thereof.

The surfactant phase also can comprise a silicon-free surfactant blend having an HLB value of about 1 to about 10. The blend is a mixture of a sufficient amount of a surfactant having a low HLB value, i.e., about 0.1 to about 10, and a sufficient amount of a surfactant having a higher HLB value, i.e., about 1 to greater than about 10, such that the surfactant blend has an HLB value of about 1 to about 10. Exemplary, but nonlimiting, nonionic surfactants having a high HLB value are listed in McCutcheon's at pages 236–246, incorporated herein by reference.

Exemplary silicon-free nonionic surfactants having an HLB value greater than about 10 are oleth-10, octylphenol or nonylphenol ethoxylated with six or more moles of ethylene oxide, steareth-10, trideceth-6, methyl gluceth-10, dodoxynol-12, ceteth-12, $C_{11-15}$ pareth-20, and mixtures thereof. The identity of the high HLB surfactant is not limited as long as the resulting surfactant phase provides a stable water-in-oil primary emulsion.

An exemplary oil-soluble silicon-based surfactant is a dimethicone copolyol, which is a dimethylsiloxane polymer having polyoxyethylene and/or polyoxypropylene side chains, such as DOW CORNING 3225C FORMULATION AID, available from Dow Corning Co., Midland, Mich. The dimethicone copolyol has about 15 or fewer ethylene oxide and/or propylene oxide monomer units, in total, in the side chains. Dimethicone copolyols conventionally are used in conjunction with silicones because the oil-soluble, silicon-based surfactants are extremely soluble in a volatile or a nonvolatile silicone compound, are extremely insoluble in water, and have a low skin irritancy potential.

Another exemplary, but nonlimiting, oil-soluble, silicon-based surfactant is an alkyl dimethicone copolyol, such as cetyl dimethicone copolyol available commercially as ABIL® EM 90 from Goldschmidt Chemical Corporation, Hopewell, Va. The alkyl dimethicone copolyols have the structure:

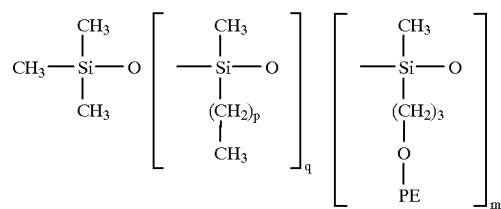

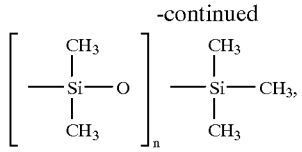

wherein p is a numeral from 7 through 17;
q is a numeral from 1 through 100;
m is a numeral from 1 through 40;
n is a numeral from 0 through 200; and
PE is $(C_2H_4O)_a(C_3H_6O)_b$—H having a molecular weight of about 250 to about 2000, wherein a and b are selected such that the weight ratio of $C_2H_4O/C_3H_6O$ is from 100/0 to 20/80.

The surfactant phase also can comprise an oil-soluble polymeric surfactant. Polymeric surfactants capable of forming water-in-oil emulsions completely cover the surface of the water droplet, are firmly anchored at the oil-water interface, the external oil phase is a good solvent for the stabilizing portion of the polymeric surfactant, and the thickness of the polymer layer on the oil side of the interface is sufficient to ensure stability. These surfactants can include repeating ethoxy, propoxy and/or similar alkylene oxide monomer units, e.g., butoxy. The oil-soluble polymeric surfactants act as surfactants and are not physically or chemically crosslinked in solution. The oil-soluble polymeric surfactants therefore are differentiated from polymeric gelling agents, such as polyacrylic acid or polymethacrylic acid.

Accordingly, exemplary oil-soluble polymeric surfactants include, but are not limited to, polyoxyethylene-polyoxypropylene block copolymers, and similar polyoxyalkylene block copolymers. The oil-soluble block copolymers typically have less than about 20% by weight of ethylene oxide. Specific nonlimiting oil-soluble polymeric surfactants include Poloxamer 101, Poloxamer 105, PPG-2-Buteth-3, PPG-3-Buteth-5, PPG-5-Buteth-7, PPG-7-Buteth-10, PPG-9-Buteth-12, PPG-12-Buteth-16, PPG-15-Buteth-20, PPG-20-Buteth-30, PPG-24-Buteth-27, PPG-28-Buteth-35, and PEG-15 Butanediol. Other useful oil-soluble polymeric surfactants are poloxamines, i.e., polyoxyethylene-polyoxypropylene block copolymers of ethylene diamine, having less than about 40% by weight ethylene oxide.

In accordance with an important feature of the present invention, the hydrophobic moiety of a silicon-free surfactant, silicon-containing surfactant or polymeric surfactant is sufficiently soluble in the oil phase such that a sufficient amount of the surfactant is present in the oil phase to stabilize the primary $W_1/O$ emulsion. In one embodiment, when the oil phase comprises a silicone compound, the surfactant phase comprises either a silicon-based surfactant, a silicon-free surfactant having a hydrophobic moiety preferably containing about ten to about fourteen carbon atoms, an oil-soluble polymeric surfactant, or a mixture thereof. If the hydrophobic moiety of the silicon-free surfactant is saturated and includes more than about 14 carbon atoms, the silicon-free surfactant is insoluble in the silicone phase and the primary $W_1/O$ emulsion is unstable. If the hydrophobic moiety includes less than about 10 carbon atoms, the primary $W_1/O$ emulsion has a tendency to coalesce, i.e., the emulsion droplets fuse to form large droplets. The amount of surfactant phase necessary to provide a primary emulsion of desired $W_1/O$ droplet diameter varies with the amount of aqueous phase in the primary emulsion and is easily determined by those skilled in the art.

II. The External Aqueous Phase

The external aqueous phase ($W_2$) of the $W_1$-O-$W_2$ multiple emulsion composition comprises water and an emulsifier in an amount of 0.1% to about 15%, and preferably about 0.5% to about 10%, by weight of the external aqueous phase; alternatively expressed as 0.001% to about 14.85%, preferably about 0.25% to about 9.9%, by weight of the $W_1$-O-$W_2$ multiple emulsion composition. To achieve the full advantage of the present invention, the external aqueous phase comprises about 1% to about 8%, by weight of the external phase of an emulsifier, alternatively expressed as about 0.5% to about 7.2% by weight of the multiple emulsion composition.

The emulsifier included in the external aqueous phase has a low affinity for the oil phase. The emulsifier therefore does not disrupt the primary $W_1$/O emulsion and avoids the formation of a simple oil-in-water emulsion. The emulsifier is present in a sufficient amount to provide a stable $W_1$-O-$W_2$ multiple emulsion composition, wherein droplets of the primary $W_1$/O emulsion are uniformly distributed throughout the external aqueous phase, and preferably remain uniformly distributed in the external aqueous phase throughout the life of the multiple emulsion composition. A sufficient amount of surfactant phase in the external aqueous phase provides $W_1$/O droplets of a sufficiently large size (i.e., about 0.5 to about 1000μ) to deposit on the skin or hair, and to resist rinsing from the skin or hair.

A $W_1$-O-$W_2$ multiple emulsion composition is tested for stability immediately after the $W_1$-O-$W_2$ multiple emulsion composition is prepared. The composition is observed under an optical microscope, and the $W_1$-O-$W_2$ multiple emulsion composition is defined as stable when droplets of the primary $W_1$/O emulsion are observed at a magnification of 50. The $W_1$-O-$W_2$ multiple emulsion composition then is examined at periodic intervals for extended stability. Preferably, the $W_1$-O-$W_2$ multiple emulsion composition is stable for the expected product life of the skin or hair care product.

The emulsifier comprises a surfactant system capable of forming stabilizing liquid crystals around the $W_1$/O droplets. The surfactant system can be a single surfactant or a blend of surfactants. In some cases, a particular surfactant cannot form a liquid crystal structure alone, but can participate in the formation of liquid crystals in the presence of a second surfactant.

The emulsifier for the external phase does not gel the external aqueous phase, but forms a stabilizing layer of lamellar liquid crystals around droplets of the internal primary $W_1$/O emulsion. This layer of liquid crystals forms a barrier film that prevents coalescence between primary emulsion droplets and precludes migration of droplet contents from the primary emulsion to the external aqueous phase. This type of an emulsion is different from conventional emulsions which rely upon the orientation of the hydrophobic and hydrophilic components of a surfactant at an oil-water interface. The formation of a layer of lamellar liquid crystals around the primary $W_1$/O emulsion can be detected by the presence of Maltese crosses viewed by optical microscopy through crossed polarizing plates or by freeze fracture electron microscopy.

As previously described, the HLB value of a surfactant is an approximate measurement of the solubility of a surfactant in water and oil. However, an HLB value is used only when the concentration of a surfactant in solution is sufficiently low such that a molecular monolayer of the surfactant is formed around droplets dispersed in a continuous phase, i.e., around the primary $W_1$/O emulsion. At higher surfactant concentrations, the surfactant can undergo a phase transition and the oil droplets then can be surrounded by a layer of lamellar liquid crystals, which can improve emulsion stability. The liquid crystals are localized at the oil/water interface and have been observed by microscopy techniques.

It is theorized, but not relied upon herein, that the layer of lamellar liquid crystals provides improved multiple emulsion stability for the following reasons. As primary $W_1$/O emulsion droplets approach one another, multiple emulsion instability occurs in two steps: (1) flocculation of the $W_1$/O droplets due to van der Waals forces, followed by (2) coalescence of the flocculated $W_1$/O droplets. The rate of droplet coalescence is related to the stability of the emulsifier film surrounding the droplets.

Liquid crystals stabilize emulsions by affecting both steps of the instability process. First, flocculation is reduced because the presence of liquid crystals modifies the attractive van der Waals forces. The presence of liquid crystal layers around the droplets significantly reduces interdroplet attraction. Additionally, the liquid crystals provide mechanical stability to the film around the primary $W_1$/O droplets, and thereby resist the film-thinning process which leads to droplet coalescence.

Exemplary classes of surfactants capable of participating in the formation of a liquid crystal structure around the primary $W_1$/O emulsion to stabilize the $W_1$-O-$W_2$ multiple emulsion composition include, but are not limited to, quaternary ammonium compounds having two long alkyl chains (i.e., $C_8$–$C_{22}$), di-long chain alkyl ($C_8$–$C_{22}$) amines, long chain fatty ($C_8$–$C_{22}$) alcohols, ethoxylated fatty alcohols, double-tailed anionic surfactants, and double-tailed phospholipids. Specific surfactants capable of participating in the formation of a stabilizing liquid crystal structure include, but are not limited to, dicetyldimonium chloride, distearyldimonium chloride, dipalmitylamine, cetyl alcohol, stearyl alcohol, steareth-2, steareth-21, dioctylsodium sulfosuccinate, phosphatidylserine, phosphatidylcholine and mixtures thereof.

The preferred surfactant systems capable of forming a stabilizing liquid crystal structure are surfactant blends that maintain the layer of lamellar liquid crystals below the Krafft temperature of the surfactants. The Krafft temperature corresponds to the melting point of the hydrocarbon chains in the surfactant, and is the temperature above which the surfactant hydrocarbon chains are liquid-like and disordered. Preferred liquid crystal-forming surfactants include, but are not limited to, a mixture of cetyl alcohol, stearyl alcohol, dicetyldimmonium chloride, stearylamidopropyldimethylamine and ceteareth-20; a mixture of distearyldimmonium chloride, cetrimonium chloride, cetyl alcohol and stearyl alcohol; and a mixture of oleth-15, cetyl alcohol and stearyl alcohol.

In a preferred embodiment, the external aqueous phase comprises water, an emulsifier and a second topically-active compound. If the $W_1$-O-$W_2$ multiple emulsion composition is designed to be a hair or skin shampoo or conditioner, the emulsifier present in the external aqueous phase can serve both as the emulsifier and the second topically-active compound.

The second topically-active compound is present in an amount of 0% to about 30%, and preferably about 0.1% to about 30%, by weight of the external aqueous phase. Alternatively expressed, the second topically-active compound is present in an amount of 0% to about 30%, and preferably about 0.05% to about 30% by weight of the $W_1$-O-$W_2$ multiple emulsion composition.

The second topically-active compound typically is a water-soluble compound. The second topically-active compound can be removed from the hair or skin with the remainder of the external aqueous phase during a rinsing step (e.g., a cleansing agent), or can remain on the hair after the rinsing step (e.g., a conditioner that is substantive to the hair). Alternatively, the $W_1$-O-$W_2$ multiple emulsion composition is a leave-on product and the second topically-active compound is allowed to remain in contact with the skin or hair.

Therefore, in addition to cleansing agents, the second topically-active compound can be a hair conditioner that is substantive to the hair, such as a quaternary ammonium compound, and therefore is not rinsed from the hair. The second topically-active compound also can be a reducing agent used in permanent waving, such as ammonium bisulfite, ammonium sulfate, ammonium sulfite, cysteamine, ammonium thioglycolate, cysteine, cysteine hydrochloride, ethanolamine thioglycolate, hydroquinone, glyceryl thioglycolate, mercaptopropionic acid, potassium metabisulfite, potassium sulfite, potassium thioglycolate, sodium bisulfite, sodium hydrosulfite, sodium hydroxymethane sulfonate, sodium metabisulfite, sodium sulfite, sodium thioglycolate, thioglycerin, thioglycolic acid, thiolactic acid, thiosalicylic acid, or mixtures thereof. In addition, a reducing agent can be the first topically-active compound, when the second topically-active compound is a hair cleanser.

The external aqueous phase also can include optional ingredients traditionally included in topically-applied compositions, such as fragrances, antioxidants, detackifying agents, preservatives or dyes.

A $W_1$-O-$W_2$ multiple emulsion composition of the present invention therefore can be a liquid composition having a viscosity of about 1 to about 15,000 cps, as measured on a Brookfield Viscometer using a #4 spindle at a speed of 20 rpm. For a hair care composition, the composition preferably has a viscosity of about 100 to about 10,000 cps. To achieve the full advantage of the present invention, the $W_1$-O-$W_2$ multiple emulsion composition has a viscosity of about 1,000 to about 9,000 cps.

The $W_1$-O-$W_2$ multiple emulsion also can be a cream-like composition having a viscosity of about 50,000 to about 1,200,000 cps, as measured on a Brookfield Viscometer using a T-BAR spindle at a speed of 2.5 rpm. The relatively high viscosity can be achieved by the addition of a gelling agent, preferably a nonpolymeric gelling agent, or can arise due to the identity and amount of ingredients in the $W_1$-O-$W_2$ multiple emulsion composition.

The $W_1$-O-$W_2$ multiple emulsion compositions typically are prepared by a two-step process. In the two-step process, the primary water-in-oil ($W_1$/O) emulsion is manufactured first, then is dispersed in the external aqueous phase ($W_2$). The second step of the two-step process emulsifies the primary $W_1$/O emulsion. This two-step manufacturing method allows for the preparation of an internal aqueous phase ($W_1$) different in composition from the external aqueous phase ($W_2$).

In the manufacture of the primary $W_1$/O emulsion, the surfactant phase is admixed with the oil phase, then the aqueous phase is dispersed in the combined surfactant and oil phases under high shear conditions and preferably in a homogenizer (e.g., about 17,000 rpm in an IKA Homogenizer, available from IKA Laboratories, Cincinnati, Ohio). Primary emulsions that were homogenized provided smaller particle size droplets of the internal aqueous phase ($W_1$) (i.e., about 1μ to about 75μ in diameter), which were more uniform in size. Primary emulsions that were homogenized therefore had increased stability.

The resulting primary $W_1$/O emulsion then is dispersed in the external aqueous phase ($W_2$) using low shear mixing (e.g., about 130 rpm on a bench scale mixer). Intensive, high shear mixing during this manufacturing step has a tendency to destroy the primary emulsion and release the contents of the internal $W_1$ aqueous phase.

The two-step manufacturing method also allows a formulator to prepare different primary $W_1$/O emulsions, i.e., primary emulsions that incorporate different topically-active compounds into the internal aqueous phase. Then, the $W_1$/O primary emulsions each can be converted into a $W_1$-O-$W_2$ multiple emulsion composition having an external aqueous phase ($W_2$) of the same composition. The two $W_1$-O-$W_2$ compositions then can be admixed to provide a multiple emulsion composition incorporating different primary $W_1$/O emulsions having different topically-active compounds which perform different or complementary functions.

The following examples are illustrative of the primary $W_1$/O emulsions and the $W_1$-O-$W_2$ multiple emulsion compositions of the present invention. However, the present invention is not limited to the specific examples set forth below. In the following examples all amounts of the various ingredients are expressed by weight percentages unless otherwise specified.

As demonstrated in the following examples, the $W_1$-O-$W_2$ multiple emulsion compositions of the present invention were phase-stable for at least a sufficient time to detect the $W_1$-O-$W_2$ multiple emulsion by an optical microscope. It is within the skill of persons in the art to optimize the identity of composition ingredients and weight percentages to provide $W_1$-O-$W_2$ multiple emulsion compositions that are phase-stable over the expected life of the composition. The $W_1$-O-$W_2$ multiple emulsion compositions also were moderately viscous liquids to creams; were easy to apply; and effectively delivered the topically-active compounds to the skin or hair. Each of the following examples was prepared by the above-described two-step method.

The following Examples 1–29 illustrate $W_1$-O-$W_2$ multiple emulsion compositions wherein the first topically-active compound in the internal $W_1$ aqueous phase is a hair fixative resin and the second topically-active compound in the external $W_2$ aqueous phase is a cationic hair conditioner or an anionic hair cleanser. The cationic surfactant systems present in the external aqueous phase ($W_2$) of Examples 1–29 form a layer of lamellar liquid crystals around the primary $W_1$/O emulsion to stabilize the $W_1$-O-$W_2$ multiple emulsion compositions.

In addition to Examples 1–29, numerous other combinations of first and second topically-active compounds are envisioned. For example, if the second topically-active compound is a conditioner, the first topically-active compound can be a true bodifier (e.g., a styling aid resin), a curling iron-activated styling aid, a protein (e.g., hydrogenated wheat protein or hydrolyzed keratin protein), a sunscreen, an optical brightener (e.g., 2-pyrrolidone-5-carboxylic acid), a humectant, or a water-soluble or water-dispersible hair dye.

If the second topically-active ingredient is a skin cleanser, the first topically-active ingredient can be a skin care product for dry skin (e.g., glycerin, propylene glycol, sorbitol, proline, urea, hyaluronate of dimethylsilanol, allantoin, aloe vera, pyrrolidone carboxylic acid or hydrolyzing collagen) or for oily skin (e.g., provitamin $B_5$).

In accordance with an important feature of the present invention, incompatible compounds can be incorporated as the first and second topically-active compounds because the incompatible compounds do not come in contact in the $W_1$-O-$W_2$ multiple emulsion composition. For example, if the second topically-active compound is a cleanser (e.g., an anionic surfactant), the first topically-active compound can be a hair conditioner (e.g., a cationic surfactant), a hair fixative, a sunscreen, an optical brightener, a hair dye, a deodorant, a skin care product, a humectant, or a bacteriocide or other topical medicament.

Exemplary, but non-limiting, combinations of first and second topically-active compounds in a $W_1$-O-$W_2$ multiple emulsion composition of the present invention are:

| First Topically-Active Compound | Second Topically-Active Compound |
|---|---|
| Neutralizer for reducing agents | Reducing agent for permanent wave |
| Reducing Agent for Permanent Wave | Hair Cleanser |
| Reducing Agent for Permanent Wave | Hair Conditioner |
| Neutralizer | Cysteamine |
| Neutralizer | Hair Conditioner |
| Hair Conditioner | Neutralizer |
| Hair Fixative Resin | Hair Fixative Resin (incompatible) |
| Topical Medicament | Topical Anesthetic |
| Skin Conditioner | Make-up Remover |
| Sunburn Reliever (e.g., vitamin F) | Skin Cleanser |
| Sunscreen | Skin Cleanser |
| Skin Conditioner | Skin Cleanser |
| Bacteriocide | Skin Cleanser |
| Deodorant | Skin Cleanser |
| Antifungal Compound | Skin Cleanser |
| Anesthetic | Skin Cleanser |
| Anti-Inflammatory | Skin Cleanser |
| Anti-Irritant | Skin Cleanser |
| Medicament | Skin Cleanser |
| Anti-Itch Compound | Skin Cleanser |
| Self-Tanning Compound | Skin Cleanser |
| Self-Tanning Compound | Skin Conditioner |
| Dermatitis Medication | Skin Cleanser |
| Hair Conditioner | Hair Cleanser |
| Hair Fixative | Hair Cleanser |
| Hair Dye | Hair Cleanser |
| Hair Dye | Hair Conditioner |
| Hair Dye | Bleaching Agent |
| Sunscreen | Hair Conditioner |
| Protein | Hair Conditioner |
| Humectant | Hair Conditioner |
| Hair Growth Promoter | Hair Cleanser |
| Hair Bleaching Agent | Hair Cleanser |
| Water-Soluble Hair Conditioner | Substantive Hair Conditioner |

EXAMPLES 1–29

Examples 1–29 were prepared in an essentially identical manner by the two-step process. The primary $W_1$/O emulsion first was prepared as described above. The primary emulsion of each example had a ratio of aqueous phase/oil phase/surfactant phase (W/O/S) summarized in Table 1. The aqueous phase $W_1$/O incorporated about 20% to about 40% by weight of the primary emulsion of a hair fixative resin, such as polyvinylpyrrolidone or the quaternized copolymer of vinylpyrrolidone and dimethylaminoethyl methacrylate, as summarized in Table 1. The surfactant phase was either cetyl dimethicone copolyol or dimethicone copolyol. The oil phase was a volatile silicone compound, i.e., cyclomethicone. It was found that primary emulsions containing about 60% by weight aqueous phase $W_1$ had excellent stability.

In Examples 1–28, the external aqueous phase ($W_2$) was Hair Conditioner Base No. 1 having the following formula:

| Hair Conditioner Base No. 1 (External Aqueous Phase) | |
|---|---|
| Ingredient | Weight %[5] |
| Soft water | q.s. to 100 |
| Citric acid (50% aqueous) | 0.185 |
| Stearamidopropyldimethylamine[1] | 0.5 |
| Propylene glycol | 0.5 |
| Dicetyldimonium chloride/PG[2] | 2.1 |
| Stearyl alcohol and Ceteareth-20 Blend[3] | 1.0 |
| Cetyl alcohol | 3.25 |
| Potassium chloride | 0.1 |
| Disodium EDTA | 0.1 |
| Methylchloroisothiazoline/ methylisothiazolinone[4] | 0.05 |
| DMDM hydantoin[4] | 0.1 |
| Potassium hydroxide (50% aqueous) | 0.033 |
| Fragrance | 0.2 |

[1]LEXAMINE S-13, available as a 100% active material, from Inolex Chemical Co., Philadelphia, PA;
[2]VARISOFT 432PG, available as a 68% active material, from Sherex Chemical Co., Dublin, OH, to provide 1.43% active material in the final formulation;
[3]PROMULGEN G, available as a 100% active blend, from Amerchol Corp., Edison, NJ;
[4]preservatives; and
[5]based on the weight raw material added to the hair conditioner base.

In Example 29, the external aqueous phase was Hair Conditioner Base No. 2 having the following formula:

| Hair Conditioner Base No. 2 (External Aqueous Phase) | |
|---|---|
| Ingredient | Wt. %[5] |
| Soft water | q.s. to 100 |
| Citric acid (50% aqueous) | 0.02 |
| Hydroxyethylcellulose | 0.3 |
| Distearyldimonium chloride[6] | 1.1 |
| Cetrimonium chloride[7] | 1.2 |
| Cetyl/stearyl alcohol[8] | 1.9 |
| Dyes | 0.0008 |
| Potassium chloride | 0.3 |
| Disodium EDTA | 0.01 |
| Methylchloroisothiazoline/ methylisothiazolinone[4] | 0.05 |
| DMDM hydantoin[4] | 0.2 |
| Fragrance | 0.2 |

[6]AROSURF ® TA-100, available as a 100% active material, from Witco Corp., NY, NY;
[7]BARQUAT CT-29, available as a 30% active material, from Lonza Inc., Fairlawn, NJ, to provide 0.57% active material in the final formulation; and
[8]available as a 100% active material, from Witco Corp., NY, NY.

The primary $W_1$/O emulsion was added to the external phase, with moderate stirring, in an amount of 4.5% to 55% by weight, based on the final weight of the $W_1$-O-$W_2$ multiple emulsion composition.

In particular, the $W_1$-O-$W_2$ multiple emulsion compositions of Examples 1–28 were manufactured as follows. Hair Conditioner Base No. 1 was prepared by heating the soft water (i.e., tap water softened by passage through an ion exchange column) to about 155 to 160° F., then adding the citric acid, stearamidopropyldimethylamine, and propylene glycol to the heated water. Next, the dicetyldimonium chloride/PG was added, and the resulting mixture was stirred for 5 minutes. When the mixture was homogeneous, the stearyl alcohol/ceteareth-20 blend was added to the mixture at a temperature above 145° F. The cetyl alcohol was added next, and the resulting mixture was stirred at high speed (i.e., about 130 rpm on a production scale mixer).

After all the ingredients were dispersed, mixing was continued for 30 minutes at 155° F. Then, the mixture was cooled to 130–135° F., followed by the addition of potassium hydroxide (diluted 1:8 with soft water). In a separate container, the potassium chloride and disodium EDTA were completely dissolved in 120° F. soft water, then, at 117–122° F., the salt solution was slowly added to the batch mixture. After cooling the resulting mixture, i.e., Hair Conditioner Base No. 1, to 110° F. or less, the primary $W_1/O$ emulsion, preservatives and fragrance were added to the mixture. The resulting $W_1$-O-$W_2$ multiple emulsion composition was cooled to 100–105° F., and low shear mixing was continued for about 30 minutes. Finally, the pH was adjusted to about 4.5 to about 6.1 with liquid citric acid or potassium hydroxide. Alternatively, the primary $W_1/O$ emulsion can be incorporated into the mixture after pH adjustment. The composition of Example 29 was prepared in a similar two-step method.

The following Table I illustrates Examples 1–29 wherein different parameters with respect to the primary $W_1/O$ emulsion and the external aqueous phase ($W_2$) were varied. Examples 1 and 2 are control examples in which cyclomethicone was incorporated directly into the hair conditioner base. The presence of a $W_1$-O-$W_2$ multiplpe emulsion was confirmed by optical microscopy.

TABLE 1

| EXAMPLE | % SILICONE[9] | W/O/S[10] | SURFACTANT[11] | RESIN[14] | REMARKS |
|---|---|---|---|---|---|
| 1 (comparative) | 1.8 | — | — | — | Hair Conditioner Base No. 1 (control) |
| 2 (comparative) | 3.0 | — | — | — | Hair Conditioner Base No. 1 with more cyclomethicone (control) |
| 3 | 1.8 | 46/46/8 | Cetyl Dimethicone Copolyol[12] | — | Multiple emulsion observed under a light microscope |
| 4 | 1.8 | 60/30/10H[17] | Cetyl Dimethicone Copolyol[12] | Polyvinylpyrrolidone[15] (1.1%) | Curl retention (qualitative) was noted on hair tresses, resin coating felt on hair |
| 5 | 3.0 | 60/30/10H | Cetyl Dimethicone Copolyol[12] | Polyvinylpyrrolidone[15] (1.8%) | Resin coating felt on hair; stable for 3 months[18] ; weak set retention of tresses[19] |
| 6 | 4.0 | 60/30/10H | Cetyl Dimethicone Copolyol[12] | Polyvinylpyrrolidone[15] (2.4%) | Identical set retention (qualitative) as Example 5 |
| 7 (comparative) | 3.0 | — | Cetyl Dimethicone Copolyol[12] | Polyvinylpyrrolidone[15] | Components added separately, no primary emulsion formed; set retention less than Example 5 |
| 8 | 4.5 | 60/30/10H | Cetyl Dimethicone Copolyol[12] | Polyvinylpyrrolidone[15] (2.7%) | Tress curl retention improved over Example 5 |
| 9 | 3.0 | 50/40/10 | Cetyl Dimethicone Copolyol[12] | Quaternized copolymer of vinylpyrrolidone and dimethylaminoethyl methacrylate (Polyquaternium 11)[16] (0.75%) | Set retention greater than polyvinylpyrrolidone (qualitative) of Example 5; stable for 3 months |
| 10 | 4.0 | 50/40/10 | Cetyl Dimethicone Copolyol[12] | Quaternized copolymer of vinylpyrrolidone and dimethylaminoethyl methacrylate (Polyquaternium 11)[16] (0.90%) | Slightly better set retention than Example 9 (qualitative); stable for 3 months |
| 11 | 3.0 | 70/20/10 UH | Cetyl Dimethicone Copolyol[12] | Quaternized copolymer of vinylpyrrolidone and dimethylaminoethyl methacrylate (Polyquaternium 11)[16] (2.1%) | Salon test[20]; wetcomb poorer than control (Example 1) hold and set retention identical to control performance: curl retention significantly better than control; stable for 3 months |
| 12 | 3.0 | 70/20/10H | Cetyl Dimethicone Copolyol[12] | Quaternized copolymer of vinylpyrrolidone and dimethylaminoethyl methacrylate (Polyquaternium 11)[16] (2.1%) | Salon test: wetcomb poorer than control hold and set retention greater than control performance: curl retention significantly better than Example 11; stable for 3 months |
| 13 (comparative) | 3.0 | 70/20/10 | Cetyl Dimethicone Copolyol[12] | Quaternized copolymer of vinylpyrrolidone and dimethylaminoethyl methacrylate (Polyquaternium 11)[16] (2.1%) | Components added separately sensory performance poorer than Example 14 |
| 14 | 3.0 | 70/20/10H | Cetyl Dimethicone Copolyol[12] | Quaternized copolymer of vinylpyrrolidone and dimethylaminoethyl methacrylate (Polyquaternium 11)[16] (2.1%) | Sensory performance greater than Example 13 |
| 15 (comparative) | 3.0 | 80/17/3 | Dimethicone copolyol[13] | Quaternized copolymer of vinylpyrrolidone and dimethylaminoethyl methacrylate (Polyquaternium 11)[16] (2.8%) | Components added separately salon: observed poorer performance compared to Ex. 16 |
| 16 | 3.0 | 80/17/3H | Dimethicone copolyol[13] | Quaternized copolymer of vinylpyrrolidone and dimethylaminoethyl methacrylate (Polyquaternium 11)[16] (2.8%) | Salon test: no difference in hold/curl retention compared to Ex. 9, stable for about 2 months |
| 17 (comparative) | 1.8 | 80/17/3 | Dimethicone copolyol[13] | Quaternized copolymer of vinylpyrrolidone and dimethylaminoethyl methacrylate (Polyquaternium 11)[16] (1.7%) | Components added separately |
| 18 | 1.8 | 80/17/3H | Dimethicone copolyol[13] | Quaternized copolymer of vinylpyrrolidone and dimethylaminoethyl methacrylate (Polyquaternium 11)[16] (1.7%) | Added as emulsion, significant increase in composition viscosity compared to Example 17 |

TABLE 1-continued

| EXAMPLE | % SILICONE[9] | W/O/S[10] | SURFACTANT[11] | RESIN[14] | REMARKS |
|---|---|---|---|---|---|
| 19 (comparative) | 1.8 | 85/10/5 | Dimethicone copolyol[13] | Quaternized copolymer of vinylpyrrolidone and dimethylaminoethyl methacrylate (Polyquaternium 11)[16] (3.1%) | Components added separately |
| 20 | 1.8 | 85/10/5H | Dimethicone copolyol[13] | Quaternized copolymer of vinylpyrrolidone and dimethylaminoethyl methacrylate (Polyquaternium 11)[16] (3.1%) | Viscosity 6000 cps, salon study 4 of 6 models had worse curl retention than identical composition using cetyl dimethicone copolyol (Example 13), stability about 45 days |
| 21 | 1.8 | 85/10/5H | Cetyl Dimethicone Copolyol[12] | Quaternized copolymer of vinylpyrrolidone and dimethylaminoethyl methacrylate (Polyquaternium 11)[16] (3.1%) | Viscosity 1080 cps, stability greater than 45 days |
| 22 | 3.0 | 85/10/5H | Dimethicone Copolyol[13] | Quaternized copolymer of vinylpyrrolidone and dimethylaminoethyl methacrylate (Polyquaternium 11)[16] (5.1%) | Salon study: worse combing but better curl than control Example 1; stability greater than one month |
| 23 | 3.0 | 85/10/5H | Cetyl Dimethicone Copolyol[12] | Quaternized copolymer of vinylpyrrolidone and dimethylaminoethyl methacrylate (Polyquaternium 12)[16] (5.1%) | Salon study: worse combing, but better curl retention after 4 to 5 hours; stability greater than one month |
| 24 | 5.0 | 85/10/5H | Cetyl Dimethicone Copolyol[12] | Quaternized copolymer of vinylpyrrolidone and dimethylaminoethyl methacrylate (Polyquaternium 11)[16] (8.5%) | Stability greater than 12 days |
| 25 | 5.5 | 85/10/5H | Cetyl Dimethicone Copolyolhu 12) | Quaternized copolymer of vinylpyrrolidone and dimethylaminoethyl methacrylate (Polyquaternium 11)[16] (9.35%) | Stability greater than 2 days |
| 26 | 1.8 | 87/10/3H | Dimethicone Copolyol[13] | Quaternized copolymer of vinylpyrrolidone and dimethylaminoethyl methacrylate (Polyquaternium 11)[16] (3.1%) | Stability sbout 45 days |
| 27 | 3.0 | 70/20/10H | Cetyl Dimethicone Copolyol[12] | Vinylpyrrolidone/methacrylamidopropyltrimethylammonium chloride copolymer (Polyquaternium 28)[21] (2.1%) | Stability greater than 7 dsys |
| 28 | 3.0 | 70/20/10H | Cetyl Dimethicone Copolyol[12] | PVP/Dimethylaminoethyl-methacrylate Copolymer[22] (2.1%) | Stability greater than 7 days |
| 29[23] | 3.0 | 85/10/5H | Cetyl Dimethicone Copolyol[12] | Quaternized copolymer of vinylpyrrolidone and dimethylaminoethyl methacrylate (Polyquatemium 11)[16] (5.1%) | Treated tresses exhibited extra body in salon tests, stability greater than 5 days |

[9]% volatile silicone (cyclomethicone) in the final $W_1O$—$W_2$ multiple emulsion composition or control;
[10]weight ratio of water phase (W) to volatile oil phase (O) to surfactant phase (S) in the primary $W_1O$ emulsion;
[11]surfactant present in the surfactant phase of the primary $W_1/O$ emulsion;
[12]ABIL ® EM-90, available as a 100% active compound from Goldschmidt Chemical Corporation, Hopewell, VA;
[13]SILWET Surfactant L-7622, available as a 100% active compound from OSi Specialties, Inc., Tarrytown, NY;
[14]Hair fixative resin present in the primary $W_1/O$ emulsion as the first topically-active compound, and the % by weight of the hair fixative resin in the $W_1$—O—$W_2$ multiple emulsion composition;
[15]PVP K-30 (M.W. 38,000), available from ISP Corp., Wayne, NJ, and added as a 30% aqueous solution;
[16]GAFQUAT 755N (M.W. 1,000,000), available from ISP Corp., Wayne, NJ, as a 20% aqueous solution;
[17]H: homogenized;
UH: unhomogenized;
[18]sample stability tested at room temperature;
[19]comparison to control sample of Example 1 unless otherwise noted;
[20]salon tests were performed on six models;
[21]GAFQUAT HS-100 (M.W. 1,000,000), available from ISP Chemicals Inc., Wayne, NJ, as a 20% aqueous solution;
[22]COPOLYMER 845 (M.W. 1,000,000), available from ISP Chemicals, Inc., Wayne, NJ, as a 20% aqueous solution; and
[23]the external aqueous phase was the cationic surfactant-based Hair Conditioner Base No. 2.

Various compositions summarized in Table I were applied to virgin brown hair tresses, available from DeMeo Bros., New York, N.Y. The compositions were worked into the hair, then rinsed from the hair. The hair tresses then were dried. The hair tresses were examined visually. Salon tests on six human models also were conducted. The technicians empirically rated hair treated with the $W_1$-O-$W_2$ multiple emulsion compositions, and the results were averaged.

As shown in Table I, the $W_1$-O-$W_2$ multiple emulsion compositions outperformed the comparative compositions of Examples 1, 2, 7, 13, 15, 17 and 19, wherein the ingredients were added separately as opposed to first forming a primary $W_1/O$ emulsion.

In particular, mass spectrometry indicated that cyclomethicone remained on the hair after rinsing, i.e., the primary emulsion was deposited. After drying the hair, the resin was released to impart set retention properties to the hair.

In addition, it was observed that resin was deposited on the hair. Hair treated with the compositions of Examples 11 and 12 had detectable amounts of resin deposited on the hair shaft. This was confirmed by scanning electron micrographs of hair treated with the compositions of Examples 11 and 12, compared to hair treated with a control sample (Example 2) that did not include a resin and compared to rinsed and unrinsed hair samples treated with an aqueous resin solution (0.5% by weight GAFQUAT 755N). The composition of Example 12, which was homogenized, applied a more uniform and thinner coating of resin on the hair, which is preferred.

Table I also illustrates that the $W_1$-O-$W_2$ multiple emulsion compositions of the present invention exhibit a stability of greater than 3 months (Examples 5 and 9–12) and that 55% by weight of a primary $W_1$/O emulsion can be incorporated into the $W_1$-O-$W_2$ multiple emulsion composition (Example 25).

In addition to the compositions of Examples 1–29, other $W_1$-O-$W_2$ multiple emulsion compositions were prepared which incorporated a first topically-active ingredient different from a hair styling resin. These $W_1$-O-$W_2$ compositions are illustrated in Table II as Examples 30–35. The compositions of Examples 30–35 incorporated either a water-soluble dye, a sunscreen, an optical brightener or a permanent wave composition as the first topically-active compound in the primary $W_1$/O emulsion. The compositions of Examples 30–35 were prepared by the two-step method set forth above with respect to Examples 1–29.

external aqueous phase ($W_2$) incorporating the cationic salt provided a homogeneous composition, without the formation of a precipitate. The primary $W_1$/O emulsion prevents formation of a precipitate because the oil phase separates the incompatible topically-active ingredients. The $W_1$-O-$W_2$ multiple emulsion composition of Examples 30 and 33 were stabilized by a layer of lamellar liquid crystals that formed around the primary $W_1$/O emulsion droplets.

The composition of Example 30 also effectively dyed virgin white tresses of hair. White hair tresses were not dyed by a composition wherein the anionic dye was simply admixed with the cationic quaternary ammonium compound. In this composition, the dye was not available to treat the hair because the dye interacted with the cationic quaternary ammonium compound.

Similarly, Example 33 incorporates an anionic sunscreen agent and a cationic quaternary ammonium salt. If benzophenone-4 is added directly to Hair Conditioner Base No. 1, a precipitate results. However, adding a primary $W_1$/O emulsion incorporating benzophenone-4 into the

TABLE II

| EXAMPLE | % SILICONE[9] | W/O/S[10] | SURFACTANT[11] | FIRST TOPICALLY-ACTIVE COMPOUND | EXTERNAL PHASE | REMARKS |
| --- | --- | --- | --- | --- | --- | --- |
| 30 | 1.87 | 72/18.7/9.3 | Cetyl Dimethicone Copolyol[12] | FD & C Red No. 22 (dye) 10%[25] | Hair Conditioner Base No. 1 | The composition was applied to virgin white tresses of hair. The composition of Example 31 dyed the tresses. No dye deposition observed with a control oil-in-water composition; stability at least one day[18] |
| 31 | 1.87 | 72/18.7/9.3 | Cetyl Dimethicone Copolyol[12] | Tri-K Arianor Madden Red (dye) 1%[25] | Hair Conditioner Base No. 1 | Stability greater than 6 days at room temperature and at 110° F., up to 6 days at 120° F. |
| 32 | 1.87 | 72/18.7/9.3 | Cetyl Dimethicone Copolyol[12] | Tri-K Arianor Madden Red (dye) 1% and Tri-K Arianor Steel Blue (dye) 1%[25] | Hair Conditioner Base No. 1 | Individual $W_1$ droplets including either blue or red dye were observed under an optical microscope |
| 33 | 3.44 | 74/20.7/5.3 | Cetyl Dimethicone Copolyol[12] | Benzophenone-4 (sunscreen) 5%[25] | Hair Conditioner Base No. 1 | The presence of sunscreen on trealed hair was detected by UV/visible light absorption; gas chromatography/mass spectroscopy detected about 10 ppm of sunscreen per gram of hair; stability greater than one week |
| 34 | 2.76 | 77.7/13.8/8.5 | Cetyl Dimethicone Copolyol[12] | Stilbene Derivative[26] (optical brightener) 10%[25] | Hair Conditioner Base No. 1 | Stability at least one week |
| 35 | 3.0 | 70/20/10 | Cetyl Dimethicone Copolyol[12] | Hair Reducing Base No. 1[27] (5.75% cysteamine HCl 0.5% ammonium hydroxide 1.4% ammnonium chloride) | Hair Conditioner Base No. 1 | Stability greater than 3 weeks |

[24]ABIL ® Wax 2434, available as a 100% active compound from Goldschmidt Chemical Corp., Hopewell, VA.;
[25]wt. % of first topically-active material in $W_1$;
[26]LEUCOPHOR BSB, available as a 100% active compound from Sandoz Chemicals Corp., Charlotte, NC; and
[27]Hair Reducing Base No. 1 includes:
water 84.5 (wt. %)
cysteamine HCl (75%) 11.0
ammonium hydroxide (28%) 2.5
ammonium bicarbonate 2.0.

The compositions of Examples 30 and 33 demonstrate $W_1$-O-$W_2$ multiple emulsion compositions of the present invention that incorporate incompatible first and second topically-active compounds. In Example 30, the first topically-active compound is an anionic dye and the second topically-active compound is a cationic quaternary ammonium compound. Simply admixing aqueous solutions of the anionic dye and cationic quaternary ammonium compound resulted in an immediate precipitate. However, adding the primary $W_1$/O emulsion incorporating the anionic dye to the internal $W_1$ phase prevented formation of a precipitate. The multiple emulsion composition of Example 33 was stabilized by the formation of a layer of lamellar liquid crystals around the primary $W_1$/O emulsion droplets.

The following Table III illustrates other primary $W_1$/O emulsions that have been prepared, then incorporated into Hair Conditioner Base No. 1 to provide a $W_1$-O-$W_2$ multiple emulsion composition of the present invention. Hair Conditioner Base No. 1 is a cationic composition capable of emulsifying silicone oils and destroying the primary emulsion. However, the primary $W_1/O$ emulsions were stable when emulsified into the cationic hair conditioner base under low shear conditions. Hair Conditioner Base No. 1 includes a di-long chain alkyl quaternary ammonium compound that acts as an emulsifier and participates in forming a stabilizing layer of lamellar liquid crystals around the primary $W_1/O$ emulsion droplets. Examples 1–89 also provided evidence that the water-soluble, first topically-active compound present in the internal aqueous phase remains on the hair in sufficient quantity to perform its intended function.

TABLE III

| EXAMPLE | W/O/S[10] | % SILICONE[28] | SURFACTANT[11] | INTERNAL AQUEOUS PHASE[30] |
|---|---|---|---|---|
| 36 | 70/20/10 | 20 | Cetyl Dimethicone Copolyol[12] | PVP/Dimethylaminoethylmethacrylate Copolymer[22] |
| 37 | 70/20/10 | 20 | Cetyl Dimethicone Copolyol[12] | Sodium Polystyrene Sulfonate[29] |
| 38 | 85/10/5 | 10 | Dimethicone Copolyol[13] (60%) and Laureth-4 (40%) | Polyquaternium 11[16] |
| 39 | 85/10/5 | 10 | Dimethicone Copolyol[13] (60%) and Laureth-1 (40%) | Polyquaternium 11[16] |
| 40 | 70/20/10 | 20 | Cetyl Dimethicone Copolyol[12] | Polyquaternium 28[21] |
| 41 | 60/30/10 | 30 | Cetyl Dimethicone Copolyol[12] | Polyvinylpyrrolidone[15] |
| 42 | 70/20/10 | 20 | Cetyl Dimethicone Copolyol[12] | Polyvinylmethacrylate methyl acrylate decadiene crosspolymer[32] |
| 43 | 78/16/6 | 16 | Dimethicone Copolyol[13] | Cysteamine soln., 37.5% active |
| 44 | 73/22/5 | 22 | Cetyl Dimethicone Copolyol[12] | Cysteamine soln., 37.5% active |
| 45 | 70/20/10 | 20 | Cetyl Dimethicone Copolyol[12] | Cysteamine, 8.25% active |
| 46 | 45/45/10 | 45 | Cetyl Dimethicone Copolyol[12] | Hair Reducing Base No. 2[31] |
| 47 | 45/45/10 | 45 | Dimethicone Copolyol[13] | Hair Reducing Base No. 2[31] |
| 48 | 63/27/10 | 27 | Dimethicone Copolyol[13] | Hair Reducing Base No. 2[31] |
| 49 | 63/27/10 | 27 | Cetyl Dimethicone Copolyol[12] | Hair Reducing Base No. 2[31] |
| 50 | 45/45/10 | 45 | Cetyl Dimethicone Copolyol[12] | Hair Reducing Base No. 2[31] |
| 51 | 45/45/10 | 45 | Dimethicone Copolyol[13] | Hair Oxidizing Base (2.2% hydrogen peroxide) |
| 52 | 63/27/10 | 27 | Dimethicone Copolyol[13] | Hair Oxidizing Base (2.2% hydrogen peroxide) |
| 53 | 63/27/10 | 27 | Cetyl Dimethicone Copolyol[12] | Hair Oxidizing Base (2.2% hydrogen peroxide) |
| 54 | 70/20/10 | 20 | Cetyl Dimethicone Copolyol[12] | Hair Oxidizing Base (2.2% hydrogen peroxide) |
| 55 | 70/20/10 | 20 | Cetyl Dimethicone Copolyol[12] | 1% aqueous red dye solution (Tri-K Arianor Madder Red) |
| 56 | 70/20/10 | 20 | Cetyl Dimethicone Copolyol[12] | 1% aqueous yellow dye solution (Tri-K Arianor Straw Yellow) |
| 57 | 70/20/10 | 20 | Cetyl Dimethicone Copolyol[12] | 1% aqueous blue dye solution (Tri-K Arianor Steel Blue) |
| 58 | 70/20/10 | 20 | Dimethicone Copolyol[13] | 1% aqueous red dye solution (Tri-K Arianor Madder Red) |
| 59 | 70/20/10 | 20 | Dimethicone Copolyol[13] | 1% aqueous yellow dye solution (Tri-K Arianor Straw Yellow) |
| 60 | 82/10/8 | 10 | Cetyl Copolyol[12] (50%) and Stearoxy Dimethicone (50%)[24] | FD&C Blue #1 Dye (5%) |
| 61 | 72/18.7/9.3 | 18.7 | Cetyl Dimethicone Copolyol[12] | FD&C Blue #1 Dye (10%) |
| 62 | 72/18.7/9.3 | 18.7 | Cetyl Dimethicone Copolyol[12] | FD&C Red #22 Dye (10%) |
| 63 | 7/2/1 | 20 | Cetyl Dimethicone Copolyol[12] | 1% aqueous sunscreen solution (Benzophenone-4) |
| 64 | 74/17.2/8.8 | 17.2 | Cetyl Dimethicone Copolyol[12] (60%) and Stearoxy Dimethicone (40%)[24] | 5% aqueous sunscreen solution (benzophenone-4) |
| 65 | 82.5/10.8/6.7 | 10.8 | Cetyl Dimethicone Copolyol[12] | 5% aqueous sunscreen solution (benzophenone-4) |
| 66 | 77.7/13.8/8.5 | 13.8 | Cetyl Dimethicone Copolyol[12] | 10% aqueous optical brightener solution (Stilbene derivative)[26] |
| 67 | 78.5/14/7.5 | 14 | Dimethicone Copolyol[13] | 5% aqueous protein solution (hydrolyzed keratin)[33] |
| 68 | 80.2/13.5/6.3 | 13.5 | Cetyl Dimethicone Copolyol[12] | 25% aqueous humectant solution (sodium PCA)[34] |
| 69 | 81.5/10.4/8.1 | 10.4 | Cetyl Dimethicone Copolyol[12] (55%) and Dimethicone Copolyol[35] (45%) | 25% aqueous humectant solution (sodium PCA)[34] |
| 70 | 87/9.8/3.2 | 9.8 | Cetyl Dimethicone Copolyol[12] | 25% aqueous humectant solution (sodium PCA)[34] |
| 71 | 80.5/13.3/6.2 | 13.3 | Cetyl Dimethicone Copolyol[12] | 50% humectant solution (glycerin) |
| 72 | 78/14.5/7.5 | 14.5 | Cetyl Dimethicone Copolyol[12] | 10% humectant solution (glycolic acid) |

TABLE III-continued

| EXAMPLE | W/O/S[10] | % SILICONE[28] | SURFACTANT[11] | INTERNAL AQUEOUS PHASE[30] |
|---|---|---|---|---|
| 73 | 78.7/14.2/7.1 | 14.2 | Cetyl Dimethicone Copolyol[12] | aqueous phase include 2% FD&C Red #40 dye and 13% Polyquaternium-11 hair fixative resin[16] |
| 74 | 50/40/10 | 40 | Cetyl Dimethicone Copolyol[12] | 20% aqueous solution of a hair fixative resin (Polyquaternium-11)[16] |
| 75 | 70/20/10 | 20 | Cetyl Dimethicone Copolyol[12] | 20% aqueous solution of a hair fixative resin (Polyquaternium-11)[16] |
| 76 | 70/20/10 | 20 | Cetyl Dimethicone Copolyol[12] | 20% aqueous solution of a hair fixative resin (Polyquaternium-11)[16] |
| 77 | 70/20/10 | 20 | Cetyl Dimethicone Copolyol[12] | 20% aqueous solution of a hair fixative resin (Polyquaternium-11)[16] |
| 78 | 80/17/3 | 17 | Cyclomethicone and Dimethicone Copolyol Blend[37] | 20% aqueous solution of a hair fixative resin (Polyquaternium-11)[16] |
| 79 | 85/10/5 | 10 | Dimethicone Copolyol[13] | 20% aqueous solution of a hair fixative resin (Polyquaternium-11)[16] |
| 80 | 85/10/5 | 10 | Cetyl Dimethicone Copolyol[12] | 20% aqueous solution of a hair fixative resin (Polyquaternium-11)[16] |
| 81 | 87/10/3 | 10 | Dimethicone Copolyol[13] | 20% aqueous solution of a hair fixative resin (Polyquaternium-11)[16] |
| 82 | 86.3/9.2/4.5 | 9.2 | Cetyl Dimethicone Copolyol[12] | 20% aqueous solution of a hair fixative resin (Polyquaternium-11)[16] |
| 83 | 87/10/3 | 10 | Dimethicone Copolyol[13] | 20% aqueous solution of a hair fixative resin (Polyquaternium-11)[16] |
| 84 | 78.9/14.6/6.5 | 14.6[37] (hydrocarbon) | Cetyl Dimethicone Copolyol[12] | 20% aqueous solution of a hair fixative resin (Polyquaternium-11)[16] |
| 85 | 80/12.6/7.4 | 12.6[37] (hydrocarbon) | Cetyl Dimethicone Copolyol[12] | 20% aqueous solution of a hair fixative resin (Polyquaternium-11)[16] |
| 86 | 80/12.6/7.4 | 12.6[37] (hydrocarbon) | Cetyl Dimethicone Copolyol[12] (50%) and Laureth-4 (50%) | 20% aqueous solution of a hair fixative resin (Polyquaternium-11)[16] |
| 87 | 80/10/10 | 10[38] Cetyl Dimethicone[39] (nonvolatile silicone) | ABIL WE-09[40] | D&C Red #40 Dye (2%) |
| 88 | 82/11.6/6.4 | 11.6[38] Cetyl Dimethicone[39] (nonvolatile silicone) | Cetyl Dimethicone Copolyol[12] | D&C Red #40 Dye (3%) |
| 89 | 75/18/7 | 18[38] Phenyl Trimethicone[41] (nonvolatile silicone) | Cetyl Dimethicone Copolyol[12] | Glycolic Acid (10%) |

[28] weight percent volatile silicone (cyclomethicone) or volatile hydrocarbon in the primary $W_1/O$ emulsion;
[29] FLEXAN 130, hair fixative resin, available from National Starch & Chemical Corp., Bridgewater, NJ, available as a 30% active material;
[30] first topically-active compound incorporated into the internal aqueous phase of the primary emulsion;
[31] Hair Reducing Base No. 2 includes:
water 67.4 (wt. %)
ammonium thioglycolate (60% solution) 23.0
dithioglycolate (40% solution) 5.0
ammonium hydroxide (28%) 2.1
ammonium bicarbonate 2.0
glycerin 0.5;
[32] GANTREZ ® XL-80, hair fixative resin, available from ISP Chemicals Inc., Wayne, NJ, added as a 5% active material;
[33] CROTEIN HKP, available from Croda, Inc., NY, NY, as a 50% active material;
[34] AJIDEW N-50, available from Ajinomoto U.S.A., Inc., Teaneck, NJ, as a 50% active material;
[35] DC Q2-5324, available from Dow Corning Corp., Midland, MI, as a 100% active material;
[36] AMERSIL ME358, available from Amerchol Corp., Edison, NJ, as a 100% active material;
[37] The cyclomethicone was replaced with a volatile hydrocarbon, PERMETHYL 101A, available from Presperse, Inc., South Plainfield, NJ;
[38] The cyclomethicone was replaced by a nonvolatile silicone;
[39] ABIL ® Wax 9801, available as a 100% active material from Goldschmidt Chemical Co., Hopewell, VA;
[40] a blend of polyglyceryl-4 isostearate, cetyl dimethicone copolyol and hexyl laurate, available from Goldschmidt Chemical Co., Hopewell, VA; and
[41] DOW CORNING 556 FLUID, available as a 100% active material from Dow Corning Corp., Midland, MI.

Each $W_1$-O-$W_2$ multiple emulsion composition summarized in Table III was stable for a definite time period. The multiple emulsion compositions of Examples 36–89 were not optimized for long term stability. Therefore, the stability of the multiple emulsion compositions varied with the identity and amount of composition ingredients, especially the emulsifiers, and with the manufacturing conditions. For example, by using low shear and relatively low mixing speeds (e.g., about 100 to about 200 rpm on a bench-scale mixer), the external aqueous phase was able to emulsify the primary $W_1/O$ emulsion. In every Example 36–89, the oil phase (O) of the primary emulsion isolated the first topically-active compound in the internal water phase ($W_1$) from the cationic hair conditioners present in the external aqueous phase ($W_2$).

The dye present in the compositions of Examples 55–62 and 73 dyed the hair after the cyclomethicone evaporated. The compositions of Examples 55–62 and 73 were nonstaining to skin and equipment because the dyes are not present in the external aqueous phase. $W_1/O$ primary emulsion droplets incorporating a water-soluble or water-dispersible dye was observed in magnified photographs of the compositions of Examples 55–59. Deposition of the dyes was observed by a color change in the hair after application of the composition to the hair and hair drying. Deposition of the sunscreen benzophenone-4 of Example 60 was detected on a wool swatch by measurement of the absorbance of ultraviolet light.

The compositions of Examples 87–89 utilize a nonvolatile silicone compound as the oil phase. The first topically-active compound in each composition was released by rubbing the treated hair after the treated hair was rinsed.

As previously stated, two independent $W_1$-O-$W_2$ multiple emulsion compositions having different primary $W_1$/O emulsions can be combined without commingling of internal aqueous phases until after deposition and evaporation of the volatile oil phase. This was demonstrated in a test compound and sugar. The aqueous phase was 80% by weight of the primary emulsion. The sugar was an optional ingredient included in the internal aqueous phase to match the refractive index of the aqueous phase to the refractive index of the volatile organic phase, and thereby provide a transparent primary $W_1$/O emulsion in most cases.

Admixing the aqueous phase with the solution of the volatile oil phase and the surfactant phase provided a clear, stable primary ($W_1$/O) emulsion. Table IV summarizes the final weight percent of each ingredient present in the primary emulsions of Examples 90 through 105, the final use of the composition, and the stability of the primary emulsion.

TABLE IV

| | | Internal Aqueous Phase | | | Volatile Organic Phase | Surfactant Phase | | Composition | |
|---|---|---|---|---|---|---|---|---|---|
| Ex. | % Sugar[42] | First Topically-effective compound | % Topically-effective compound | % Water | % Cyclomethicone | % Laureth-1 | % Laureth-4 | Product Type | Stability |
| 90 | 36.4 | Hyaluronic acid | 0.13 | 44.1 | 13.6 | 3.88 | 1.94 | Skin conditioner | stable |
| 91 | 29.0 | Sodium salicylate | 3.90 | 47.0 | 14.0 | 4.00 | 2.00 | Skin conditioner | stable |
| 92 | 31.5 | Urea | 7.60 | 47.1 | 9.49 | 2.70 | 1.35 | Skin conditioner | stable |
| 93 | 35.5 | 85% lactic acid | 4.90 | 45.0 | 10.2 | 2.93 | 1.46 | Skin conditioner | stable |
| 94 | 33.4 | 5% glycerin | 3.60 | 46.8 | 11.3 | 3.24 | 1.62 | Skin conditioner | stable |
| 95 | 32.2 | Vitamin C | 4.29 | 45.1 | 12.9 | 3.69 | 1.84 | water-soluble vitamin | stable |
| 96 | 35.3 | Vitamin $B_1$ | 0.59 | 45.0 | 13.4 | 3.83 | 1.92 | water-soluble vitamin | stable |
| 97 | 34.3 | Pyridoxine hydrochloride | 1.32 | 45.1 | 13.5 | 3.87 | 1.94 | water-soluble vitamin | stable |
| 98 | 37.1 | Panthenol | 1.90 | 46.3 | 10.3 | 2.95 | 1.47 | water-soluble vitamin | stable |
| 99 | 35.7 | Nicotinic acid | 0.42 | 44.5 | 13.6 | 3.88 | 1.94 | cosmetic | stable |
| 100 | 35.7 | Boric acid | 1.08 | 43.8 | 13.7 | 3.90 | 1.95 | medicament | stable |
| 101 | 34.9 | Sodium sulfactamide | 2.74 | 48.5 | 9.70 | 2.77 | 1.39 | bacteriocide | stable |
| 102 | 32.5 | Triclosan | 1.03 | 37.6 | 20.2 | 5.77 | 2.88 | bacteriocide | stable |
| 103 | 37.6 | Indomethacin | 1.90 | 43.4 | 12.8 | 2.91 | 1.43 | anti-inflammatory agent | stable |
| 104 | 39.1 | 87% bisabolol | 0.70 | 45.1 | 10.6 | 3.03 | 1.51 | anti-irritant | stable |
| 105 | 31.9 | Silver sulfadiazine | 3.30 | 36.8 | 19.6 | 5.61 | 2.81 | medicament | stable |

[42]All % are by weight of the primary $W_1$/O emulsion.

wherein two different primary emulsions were prepared. The first primary emulsion incorporated a red dye in the internal aqueous phase. The second primary emulsion incorporated a blue dye in the internal aqueous phase. Each primary emulsion was added to individual portions of an external aqueous phase to provide two independent $W_1$-O-$W_2$ multiple emulsion compositions. The two multiple emulsion compositions then were combined. The dye-containing droplets of the two primary emulsions were distinct and did not coalesce, commingle or transfer dyes when viewed through a microscope.

The following Examples 90–105 illustrate other primary $W_1$/O emulsions that have been prepared. Each of these primary emulsions can be incorporated into an external aqueous phase comprising a surfactant capable of forming a layer of lamellar liquid crystals as the emulsifier to provide a $W_1$-O-$W_2$ multiple emulsion composition of the present invention.

In Examples 90 through 105, the volatile oil phase was cyclomethicone (DOW CORNING 344 FLUID). The surfactant phase of the primary $W_1$/O emulsion was a combination of laureth-1 and laureth-4. In preparing the compositions of Examples 90 through 105, the cyclomethicone, laureth-1 and laureth-4, in a weight ratio of 70:20:10, respectively, were admixed until homogeneous. The internal aqueous phase comprised water, the first topically-active Each composition of Examples 90–105 can be incorporated in a $W_1$-O-$W_2$ multiple emulsion composition of the present invention, wherein the external aqueous phase further comprises a skin cleanser or a skin conditioner. The skin cleanser cleans the skin and is removed from the skin during a rinsing step. The skin conditioner is allowed to remain on the skin. The first topically-active compound remains on the skin to perform its intended function after evaporation of the cyclomethicone.

The compositions of the following Examples 106 and 107 are leave-on $W_1$-O-$W_2$ multiple emulsion compositions. Each composition was applied to the skin, then allowed to remain on the skin without a rinsing step. In each example, the skin care products in the external aqueous ($W_2$) phase perform their intended function upon application to the skin. After evaporation of the water in the external aqueous phase, and evaporation of the volatile oil phase of the primary $W_1$/O emulsion, the first topically-active compound, or compounds, in the aqueous phase ($W_1$) of the primary emulsion is released to contact the skin and perform its intended function.

Each $W_1$-O-$W_2$ multiple emulsion composition of Examples 106 and 107 was prepared by the above-described two-step method, wherein the primary $W_1$/O emulsion and the external aqueous phase are prepared independently, then the primary $W_1/O$ emulsion and the external aqueous phase are combined to form the multiple emulsion composition. The $W_1$-O-$W_2$ multiple emulsion compositions of Examples 106 and 107 are stabilized by a layer of lamellar liquid crystals.

EXAMPLE 106

| | |
|---|---|
| Primary $W_1/O$ emulsion | 20%[43] |
| water | 58.5%[44] |
| glycolic acid[45] | 5% |
| glycerin[45] | 12% |
| cyclomethicone[46] | 17% |
| silicon-based surfactant[12] | 7.5% |
| External aqueous ($W_2$) phase[43] | |
| Soft Water | q.s. to 100% |
| Methyl paraben[47] | 0.12% |
| Glycerin[48] | 2.4% |
| Tetrasodium ethylenediamine-tetraacetic acid | 0.08% |
| Triethanolamine | 0.8% |
| Ester blend[49] | 2.64% |
| CRODAMOL PMP[50] | 0.54% |
| $C_{12}$–$C_{15}$ alkyl benzoate | 0.264% |
| Stearic acid | 2.64% |
| Cetearyl alcohol | 0.64% |
| Cetyl palmitate | 0.44% |
| GLUCAM E-20 distearate[51] | 0.4% |
| ARLACEL 165[52] | 0.4% |
| SILICONE 593 fluid[53] | 0.08% |
| DMDM Hydantoin[47] | 0.2% |
| Fragrance | 0.08% |
| Dye | 0.00008% |

[43]percent by weight in the $W_1$-O-$W_2$ multiple emulsion composition;
[44]percent by weight in the primary ($W_1$/O) emulsion;
[45]first-topically active compound;
[46]volatile oil phase;
[47]preservative;
[48]second-topically active compound;
[49]blend of tridecyl stearate, neopentyl glycol dicaprylate/dicaparate and tridecyl trimellitate, available as a 100% active material from Lipo Chemicals, Inc., Paterson, NJ;
[50]PPG-2 myristyl ether propionate, available as a 100% active material from Croda, Inc., NY, NY;
[51]PEG-20 methyl glucose distearate, available as a 100% active material from Amerchol Corp., Edison, NJ;
[52]glyceryl stearate and PEG-100 stearate blend, available as a 100% active material from ICI Americas, Wilmington, DE; and
[53]dimethicone trimethylsiloxysilicate, available as a 100% active material from Dow Corning Corp., Midland, MI.

EXAMPLE 107

| | |
|---|---|
| Primary $W_1/O$ emulsion | 20%[43] |
| water | 48.6%[44] |
| glycerin[45] | 25% |
| red dye[45] | 1% |
| cyclomethicone[46] | 18% |
| silicon-based surfactant[12] | 7.4% |
| External aqueous ($W_2$) phase[43] | |
| Soft Water | q.s. to 100% |
| Methyl paraben[47] | 0.12% |
| Glycerin[48] | 3.2% |
| Tetrasodium ethylenediamine-tetraacetic acid | 0.08% |
| Ester blend[49] | 2.92% |
| CRODAMOL PMP[52] | 1.68% |
| GLUCATE SS[44] | 1.68% |
| PROMULGEN D[3] | 0.84% |
| GLUCAMATE SSE-20 | 0.84% |
| CASTOR WAX MP-70[56] | 0.84% |
| Cetearyl alcohol | 0.54% |
| Cetyl palmitate | 0.42% |

EXAMPLE 107 -continued

| | |
|---|---|
| SOLULAN C-24[55] | 0.28% |
| SILICONE 593 fluid[53] | 0.17% |
| Triethanolamine | 0.24% |
| Fragrance | 0.008% |
| DMDM Hydantoin[47] | 0.24% |

[54]Methyl glucose sesquistearate, available as a 100% active material from Americhol Corp., Edison, NJ;
[55]a blend of choleth-24 and ceteth-24, available as a 100% active material from Amerchol Corp., Edison, NJ; and
[56]hydrogenated castor oil, available from CasChem, Bayonne, NJ.

The compositions of Examples 106 and 107 were stable $W_1$-O-$W_2$ multiple emulsion compositions that effectively delivered the first and second topically-active compounds to the skin.

A $W_1$-O-$W_2$ multiple emulsion composition of the present invention demonstrates excellent esthetic and functional properties, such as the ability to treat the hair or skin with incompatible topically-active compounds from a single composition. The present multiple emulsion compositions also provide a more efficacious and economical delivery of water-soluble topically-active compounds. The compositions also are phase stable at room temperature for extended storage periods due to formation of a layer of lamellar liquid crystals around the primary $W_1$/O emulsion.

In addition, the present $W_1$-O-$W_2$ multiple emulsion compositions have the additional benefit of keeping a water-soluble, first topically-active compound in the internal aqueous phase from contacting individuals that apply the multiple emulsion composition, or from contacting workplace articles, such as sinks and countertops. The volatility of the oil phase of the primary emulsion also can be selected and adjusted for release of the first topically-active compound at a predetermined temperature range, e.g., at normal hair drying, at blow drying or at curling iron temperatures.

It should be understood that the foregoing detailed description is given merely by way of illustration. Obviously, many modifications and variations of the invention as hereinbefore set forth can be made without departing from the spirit and scope thereof and therefore only such limitations should be imposed as are indicated by the appended claims.

What is claimed and desired to be secured by Letters Patent is:

1. A water-in-oil-in-water multiple emulsion composition comprising:
   (a) about 40% to about 99% by weight of the composition of an external aqueous phase comprising: (i) water and (ii) about 0.1% to about 15% by weight of the external aqueous phase of a surfactant system capable of forming liquid crystals, wherein the surfactant system in the external phase is selected from the group consisting of a quaternary ammonium compound having two long alkyl ($C_8$–$C_{22}$) chains, a di-long chain alkyl ($C_8$–$C_{22}$) amine, a long chain fatty ($C_8$–$C_{22}$) alcohol, an ethoxylated fatty ($C_8$–$C_{22}$) alcohol, a double-tailed anionic surfactant, a double-tailed phospholipid, and mixtures thereof; and
   (b) about 1% to about 60% by weight of the composition of a primary emulsion, said primary emulsion comprising:
      (i) about 1% to about 95% by weight of the primary emulsion of an aqueous phase comprising a topically-effective amount of a first topically-active compound and water, (ii) about 5% to about 95% by weight of the primary emulsion of an oil phase comprising: (A) a volatile silicone compound, a nonvolatile silicone compound, a volatile hydrocarbon compound, a nonvolatile hydrocarbon compound, or a mixture thereof, and (B) a dye, and (iii) about 0.1% to about 20% by weight of the primary emulsion of a surfactant phase comprising a silicon-free surfactant or surfactant blend having an HLB value of about 10 or less, an oil-soluble silicon-based surfactant, an oil-soluble polymeric surfactant, or a mixture thereof.

2. The composition of claim 1 wherein the external aqueous phase further comprises 0% to about 30% by weight of the external aqueous phase of a second topically-active compound.

3. The composition of claim 2 wherein the first topically-active compound and the second topically-active compound are different compounds.

4. The composition of claim 2 wherein the first topically-active compound and the second topically-active compound are identical compounds.

5. The composition of claim 2 wherein the first topically-active compound and the second topically-active compound are incompatible compounds.

6. The composition of claim 2 wherein the second topically-active compound is present in an amount of about 0.1% to about 30% by weight of the external phase.

7. The composition of claim 2 wherein the second topically-active compound is selected from the group consisting of a hair conditioner, a hair cleanser, a hair fixative, a hair dye, a hair growth promoter, a permanent wave compound, a hair relaxer, a hair straightener, an oxidizing agent, an antioxidant, an optical brightener, a hair bleaching agent, a hair reducing agent, an ultraviolet light absorber, and mixtures thereof.

8. The composition of claim 7 wherein the hair dye comprises a water-soluble dye selected from the group consisting of m-aminophenol hydrochloride, p-aminophenol sulfate, 2,3-diaminophenol hydrochloride, 1,5-naphthalenediol, p-phenylenediamine hydrochloride, sodium picramate, a water-soluble cationic dye, a water-soluble anionic dye, a water-soluble FD&C dye, Blue No. 1, Blue No. 2, Red No. 3, Red No. 4, Red No. 40, a water-soluble D&C dye, Yellow No. 10, Red No. 22, Red No. 28, and pyrogallol.

9. The composition of claim 2 wherein the first topically-active compound comprises a hair fixative resin, a hair reducing agent, a protein, an oxidizing agent, a water-soluble hair dye, a sunscreen a humectant, or an optical brightener, and the second topically-active compound comprises a cationic hair conditioner or an anionic hair cleanser.

10. The composition of claim 9 wherein the hair fixative resin is selected from the group consisting of a polyvinylpyrrolidone, Polyquaternium-11, PVP/dimethylaminoethylmethacrylate copolymer, a sodium polystyrene sulfonate, a polyethylene glycol, and mixtures thereof.

11. The composition of claim 2 wherein the first topically-active compound comprises a cationic hair conditioner, and the second topically-active compound comprises an anionic cleanser.

12. The composition of claim 2 wherein the first topically-active compound comprises a neutralizer for reducing agents and the second topically-active compound comprises a reducing agent for permanent hair waving, cysteine, cysteamine, or a hair conditioner.

13. The composition of claim 2 wherein the first topically-active compound comprises a reducing agent for permanent hair waving, and the second topically-active compound comprises a hair cleanser or a hair conditioner.

14. The composition of claim 2 wherein the first topically-active compound comprises a hair conditioner, and the second topically-active compound comprises an oxidizing agent.

15. The composition of claim 2 wherein the first topically-active compound comprises a hair conditioner, a hair dye, a hair growth promoter, a hair bleaching agent, or a mixture thereof, and the second topically-active compound comprises a hair cleanser.

16. The composition of claim 2 wherein the first topically-active compound comprises a hair dye, and the second topically-active compound comprises a hair conditioner, a bleaching agent, or a mixture thereof.

17. The composition of claim 2 wherein the first topically-active compound comprises a water-soluble hair conditioner and the second topically-active compound comprises a substantive hair conditioner.

18. The composition of claim 2 wherein the first topically-active compound comprises a sunscreen, a protein, a humectant, or a mixture thereof, and the second topically-active compound comprises a hair conditioner.

19. The composition of claim 2 wherein the first topically-active compound comprises a hair dye, and the second topically-active compound comprises a hair dye.

20. The composition of claim 1 wherein the external aqueous phase is free of a polymeric gelling agent.

21. The composition of claim 1 wherein the composition is a liquid having a viscosity of about 1 to about 15,000 centipoise.

22. The composition of claim 1 wherein the composition is a cream having a viscosity of about 50,000 to about 1,200,000 centipoise and the external aqueous phase is free of a polymeric gelling agent.

23. The composition of claim 1 wherein the primary emulsion is present in the form of droplets having a diameter of about 5 to about 1000 microns.

24. The composition of claim 1 wherein the first topically-active compound is present in an amount of about 0.1% to about 30% by weight of the primary emulsion.

25. The composition of claim 1 wherein the first topically-active compound is water soluble.

26. The composition of claim 1 wherein the first topically-active compound is selected from the group consisting of a hair conditioner, a hair cleanser, a hair fixative, a hair dye, a hair growth promoter, a permanent wave compound, a hair relaxer, a hair straightener, an oxidizing agent, an antioxidant, an optical brightener, a hair bleaching agent, a hair reducing agent, an ultraviolet light absorber, and mixtures thereof.

27. The composition of claim 26 wherein the hair dye comprises a water-soluble dye selected from the group consisting of m-aminophenol hydrochloride, p-aminophenol sulfate, 2,3-diaminophenol hydrochloride, 1,5-naphthalenediol, p-phenylenediamine hydrochloride, sodium picramate, a water-soluble cationic dye, a water-soluble anionic dye, a water-soluble FD&C dye, Blue No. 1, Blue No. 2, Red No. 3, Red No. 4, Red No. 40, a water-soluble D&C dye, Yellow No. 10, Red No. 22, Red No. 28, and pyrogallol.

28. The composition of claim 1 wherein the oil phase is present in an amount of about 0.5% to about 80% by weight of the primary emulsion.

29. The composition of claim 1 wherein the oil phase comprises a volatile silicone compound.

30. The composition of claim 29 wherein the volatile silicone compound has a viscosity of about 0.5 to about 6 centistokes.

31. The composition of claim 30 wherein the cyclic volatile silicone is a cyclomethicone.

32. The composition of claim 1 wherein the oil phase comprises a volatile hydrocarbon compound having about 10 to about 30 carbon atoms.

33. The composition of claim 32 wherein the volatile hydrocarbon compound has about 12 to about 24 carbon atoms and has a boiling point at 760 mm of about 100° C. to about 250° C.

34. The composition of claim 1 wherein the oil phase comprises a nonvolatile silicone compound.

35. The composition of claim 1 wherein the oil phase comprises a nonvolatile hydrocarbon compound.

36. The composition of claim 1 wherein the oil phase comprises a volatile oil phase and a nonvolatile oil phase.

37. The composition of claim 1 wherein the surfactant phase is present in an amount of about 0.1% to about 10% by weight of the primary emulsion.

38. The composition of claim 1 wherein the surfactant phase comprises a silicon-free surfactant or surfactant blend having an HLB of about 1 to about 7.

39. The composition of claim 1 wherein the surfactant phase comprises one silicon-free surfactant having an HLB value of about 0.1 to about 10.

40. The composition of claim 1 wherein the surfactant phase comprises a silicon-free surfactant blend having an HLB value of about 1 to about 10, said surfactant blend comprising a first surfactant having an HLB value of about 0.1 to about 10 and a second surfactant having an HLB greater than about 10.

41. The composition of claim 1 wherein the surfactant phase comprises a silicon-free nonionic surfactant selected from the group consisting of a polyoxyethylene ether of a fatty ($C_6$–$C_{22}$) alcohol, a polyoxyethylene/polyoxypropylene ether of a fatty ($C_6$–$C_{22}$) alcohol, an ethyoxylated alkylphenol, a polyethylene glycol ether of methyl glucose, a polyethylene ether of sorbitol, and mixtures thereof.

42. The composition of claim 1 wherein the surfactant phase comprises an oil-soluble silicon-based surfactant.

43. The composition of claim 42 werein the silicon-based surfactant comprises a dimethicone copolyol having 15 or less total monomer units of ethylene oxide, propylene oxide or a mixture thereof, an alkyl dimethicone copolyol having the structure:

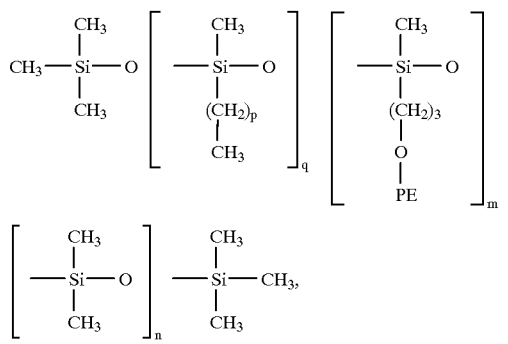

wherein p is a numeral from 7 through 17;
q is a numeral from 1 through 100;
m is a numeral from 1 through 40;
n is a numeral from 0 through 200; and PE is $(C_2H_4O)_a(C_3H_6O)_b$—H having a molecular weight of about 250 to about 2000, wherein a and b are selected such that the weight ratio of $C_2H_4O/C_3H_6O$ is from 100/0 to 20/80, or a mixture thereof.

44. The composition of claim 1 wherein the surfactant phase comprises an oil-soluble polymeric surfactant capable of forming water-in-oil emulsions and having repeating ethoxy units, propoxy units, butoxy units or combinations thereof, and includes less than 40 weight % ethoxy units.

45. The composition of claim 1 wherein the surfactant phase comprises an oil-soluble silicon-based surfactant, and the oil phase comprises a volatile silicone compound or a nonvolatile silicone compound.

46. The composition of claim 1 wherein the surfactant phase comprises a silicon-free nonionic surfactant or an oil-soluble polymeric surfactant and the oil phase comprises a volatile hydrocarbon compound or nonvolatile hydrocarbon compound.

47. The composition of claim 1 wherein the oil phase comprises a combination of a silicone compound and hydrocarbon compound, and the surfactant phase comprises a combination of a silicon-based surfactant and a silicon-free nonionic surfactant, an oil-soluble polymeric surfactant or a mixture thereof.

48. The composition of claim 1 wherein the surfactant system in the external phase is present in an amount of about 0.1% to about 15% by weight of the external phase.

49. The composition of claim 1 wherein the surfactant system in the external phase is selected from the group consisting of a mixture of cetyl alcohol, stearyl alcohol, dicetyldimmonium chloride, stearylamidopropyldimethylamine and ceteareth-20; a mixture of distearyldimmonium chloride, cetrimonium chloride, cetyl alcohol and stearyl alcohol; a mixture of oleth-15, cetyl alcohol and stearyl alcohol; and mixtures thereof.

50. The composition of claim 1 wherein the surfactant system in the external phase is selected from the group consisting of dicetyldimonium chloride, distearyldimonium chloride, dipalmitylamine, cetyl alcohol, stearyl alcohol, steareth-2, steareth-21, dioctylsodium sulfosuccinate, phosphatidylserine, phosphatidylcholine, and mixtures thereof.

51. The composition of claim 1 wherein the dye present in the oil phase of the primary emulsion is a water-insoluble dye.

52. The composition of claim 1 wherein the dye is present in a sufficient amount to affect human hair color.

53. A water-in-oil-in-water multiple emulsion composition comprising:
(a) about 50% to about 95% by weight of the composition of an external aqueous phase comprising:
(i) about 0.1% to about 30% by weight of the external aqueous phase of a second topically-active compound,
(ii) about 0.5% to about 10% by weight of the external aqueous phase of a surfactant system capable of forming liquid crystals, wherein the surfactant system in the external phase is selected from the group consisting of a quaternary ammonium compound having two long alkyl ($C_8$–$C_{22}$) chains, a di-long chain alkyl ($C_8$–$C_{22}$) amine, a long chain fatty ($C_8$–$C_{22}$) alcohol, an ethoxylated fatty ($C_8$–$C_{22}$) alcohol, a double-tailed anionic surfactant, a double-tailed phospholipid, and mixtures thereof, and
(iii) water; and
(b) about 5% to about 50% by weight of the composition of a primary emulsion, said primary emulsion comprising:

(i) about 10% to about 95% by weight of the primary emulsion of an aqueous phase comprising (A) water and (B) about 0.1% to about 30% by weight of the primary emulsion of a first topically-active compound;

(ii) about 0.5% to about 80% by weight of the primary emulsion of an oil phase comprising: (A) a volatile silicone compound, a nonvolatile silicone compound, a volatile hydrocarbon compound, a nonvolatile hydrocarbon compound, or a mixture thereof and (B) a dye; and (iii) about 0.1% to about 15% by weight of the primary emulsion of a surfactant phase comprising a silicon-free surfactant or surfactant blend having an HLB value of about 1 to about 7, an oil-soluble silicon-based surfactant, an oil-soluble polymeric surfactant, or a mixture thereof.

54. A water-in-oil-in-water multiple emulsion composition comprising:

(a) about 40% to about 99% by weight of the composition of an external aqueous phase comprising: (i) water and (ii) about 0.001% to about 14.85% by weight of the composition of a surfactant system capable of forming liquid crystals; wherein the surfactant system in the external phase is selected from the group consisting of a quaternary ammonium compound having two long alkyl ($C_8$–$C_{22}$) chains, a di-long chain alkyl ($C_8$–$C_{22}$) amine, a long chain fatty ($C_8$–$C_{22}$) alcohol, an ethoxylated fatty ($C_8$–$C_{22}$) alcohol, a double-tailed anionic surfactant, a double-tailed phospholipid, and mixtures thereof, and (b) about 1% to about 60% by weight of the composition of a primary emulsion, said primary emulsion comprising:

(i) about 0.01% to about 57% by weight of the composition of an aqueous phase comprising water and about 0.001% to about 17.1% by weight of the composition of a first topically-active compound, (ii) about 0.005% to about 57% by weight of the composition of an oil phase comprising: (A) a volatile silicone compound, a nonvolatile silicone compound, a volatile hydrocarbon compound, a nonvolatile hydrocarbon compound, or a mixture thereof and (B) a dye, and (iii) about 0.001% to about 12% by weight of the composition of a surfactant phase comprising a silicon-free surfactant or surfactant blend having an HLB value of about 10 or less, an oil-soluble silicon-based surfactant, an oil-soluble polymeric surfactant, or a mixture thereof.

55. The composition of claim 54 wherein the external phase further comprises 0% to about 30% by weight of the composition of a second topically-active compound.

* * * * *

UNITED STATES PATENT AND TRADEMARK OFFICE
CERTIFICATE OF CORRECTION

PATENT NO. : 5,942,216
DATED : August 24, 1999
INVENTOR(S) : Herb et al.

It is certified that error appears in the above-indentified patent and that said Letters Patent is hereby corrected as shown below:

On the cover page of the above-identified patent, in line 4 of the Inventors' Section, after the word "Palatine," please insert:

-- Gerald P. Newell, Hoffman Estates; Trefor A. Evans,

Lombard; Kimberly Kamis, Glenview; Richard M. Brucks, Chicago -- .

Signed and Sealed this

Seventh Day of March, 2000

Attest:

Q. TODD DICKINSON

*Attesting Officer*  *Commissioner of Patents and Trademarks*